(12) United States Patent
Woehr et al.

(10) Patent No.: US 8,758,296 B2
(45) Date of Patent: *Jun. 24, 2014

(54) SAFETY SYRINGES

(75) Inventors: Kevin Woehr, Felsberg (DE); Juergen Fuchs, Bad Emstal (DE)

(73) Assignee: B. Braun Melsungen AG, Melsungen (DE)

( * ) Notice: Subject to any disclaimer, the term of this patent is extended or adjusted under 35 U.S.C. 154(b) by 1019 days.

This patent is subject to a terminal disclaimer.

(21) Appl. No.: 12/433,553

(22) Filed: Apr. 30, 2009

(65) Prior Publication Data

US 2009/0216188 A1    Aug. 27, 2009

Related U.S. Application Data

(62) Division of application No. 10/769,067, filed on Jan. 30, 2004, now Pat. No. 7,530,966.

(30) Foreign Application Priority Data

Feb. 27, 2003    (DE) .............................. 203 03 231 U

(51) Int. Cl.
*A61M 5/00*    (2006.01)
(52) U.S. Cl.
USPC ........................................................ 604/110
(58) Field of Classification Search
CPC .............. A61M 5/178; A61M 5/3129; A61M 5/31511; A61M 5/31515; A61M 5/322; A61M 5/3234; A61M 5/326; A61M 5/508; A61M 2005/31516; A61M 2005/323; A61M 2005/3235; A61M 2005/3238; A61M 2005/3239; A61M 2005/3264
USPC .................. 604/110, 187, 192, 195, 197, 198
See application file for complete search history.

(56) References Cited

U.S. PATENT DOCUMENTS

| 3,598,120 A | 8/1971 | Mass |
| 4,950,241 A | 8/1990 | Ranford |

(Continued)

FOREIGN PATENT DOCUMENTS

| DE | 39 25 834 A1 | 2/1991 |
| DE | 43 14 395 C1 | 12/1994 |

(Continued)

OTHER PUBLICATIONS

Notice of Allowance mailed Mar. 2, 2009 from related U.S. Appl. No. 10/769,067.

(Continued)

*Primary Examiner* — Andrew Gilbert
(74) *Attorney, Agent, or Firm* — Klein, O'Neill & Singh, LLP

(57) ABSTRACT

Syringes are disclosed herein incorporating a variety of safety mechanisms for protecting the users from accidental needle stick. In certain embodiments, the syringes incorporate retractable carriages that can be retracted into the syringe barrels by engaging with the plungers. The carriages are configured to receive different needle hubs having any number of needle sizes. In certain other embodiments, the carriages are spring loaded so that as the plungers disengage the carriages from the syringe barrels, the springs automatically retract the needles into the barrels. Still in certain other embodiments, needle hubs with spring loaded needles are used with the syringes. The needles are retracted into the barrels when the plungers activate certain mechanisms incorporated into the hubs to thereby release the needles.

24 Claims, 11 Drawing Sheets

(56) References Cited

U.S. PATENT DOCUMENTS

| | | | |
|---|---|---|---|
| 5,053,010 A * | 10/1991 | McGary et al. | 604/110 |
| 5,084,018 A * | 1/1992 | Tsao | 604/110 |
| 5,188,599 A | 2/1993 | Botich et al. | |
| 5,378,240 A | 1/1995 | Curie et al. | |
| 5,385,551 A * | 1/1995 | Shaw | 604/110 |
| 5,395,346 A | 3/1995 | Maggioni | |
| 5,632,733 A | 5/1997 | Shaw | |
| 5,716,341 A | 2/1998 | Saito | |
| 5,782,804 A | 7/1998 | McMahon | |
| 5,785,687 A | 7/1998 | Saito | |
| 5,817,058 A | 10/1998 | Shaw | |
| 5,843,034 A | 12/1998 | Redfern et al. | |
| 5,984,897 A | 11/1999 | Petersen et al. | |
| 5,989,220 A | 11/1999 | Shaw et al. | |
| 5,997,511 A * | 12/1999 | Curie et al. | 604/195 |
| 6,010,486 A | 1/2000 | Carter et al. | |
| 6,015,438 A | 1/2000 | Shaw | |
| 6,090,077 A * | 7/2000 | Shaw | 604/195 |
| 6,156,014 A | 12/2000 | Petersen et al. | |
| 6,179,812 B1 | 1/2001 | Botich et al. | |
| 6,193,695 B1 | 2/2001 | Rippstein, Jr. | |
| 6,196,997 B1 * | 3/2001 | Saito | 604/110 |
| 6,221,052 B1 | 4/2001 | Caizza et al. | |
| 6,676,641 B2 | 1/2004 | Woodard, Jr. et al. | |
| 6,878,131 B2 | 4/2005 | Novacek et al. | |
| 6,994,690 B2 * | 2/2006 | Kiehne | 604/110 |
| 7,530,966 B2 * | 5/2009 | Woehr et al. | 604/110 |
| 2004/0006313 A1 | 1/2004 | Chian | |

FOREIGN PATENT DOCUMENTS

| | | |
|---|---|---|
| EP | 0 979 660 A1 | 2/2000 |
| EP | 1 374 936 A1 | 1/2004 |
| WO | WO 95/27524 | 10/1995 |
| WO | WO 01/42104 A1 | 6/2001 |
| WO | WO 2004/004808 A1 | 1/2004 |

OTHER PUBLICATIONS

Office Action mailed Sep. 23, 2008 from related U.S. Appl. No. 10/769,067.

Final Office Action mailed Apr. 8, 2008 from related U.S. Appl. No. 10/769,067.

Office Action mailed Nov. 21, 2007 from related U.S. Appl. No. 10/769,067.

Final Office Action mailed Mar. 28, 2007 from related U.S. Appl. No. 10/769,067.

Office Action mailed Dec. 5, 2006 from related U.S. Appl. No. 10/769,067.

Office Action mailed Oct. 11, 2006 from related U.S. Appl. No. 10/769,067.

Office Action mailed Feb. 13, 2009 from related U.S. Appl. No. 11/707,846.

Final Office Action mailed Sep. 24, 2008 from related U.S. Appl. No. 11/707,846.

Office Action mailed May 16, 2008 from related U.S. Appl. No. 11/707,846.

Office Action mailed Feb. 26, 2008 from related U.S. Appl. No. 11/707,846.

* cited by examiner

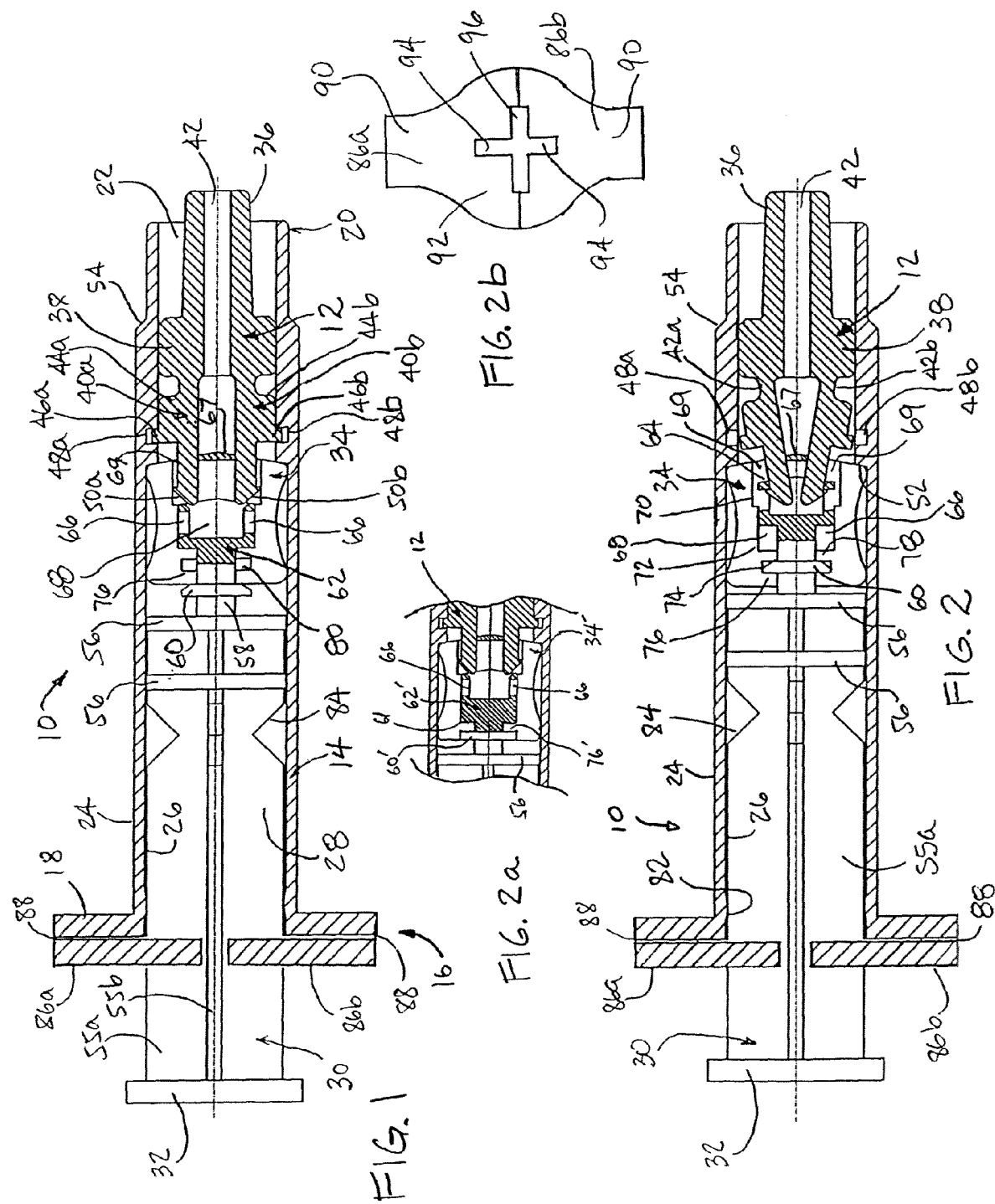

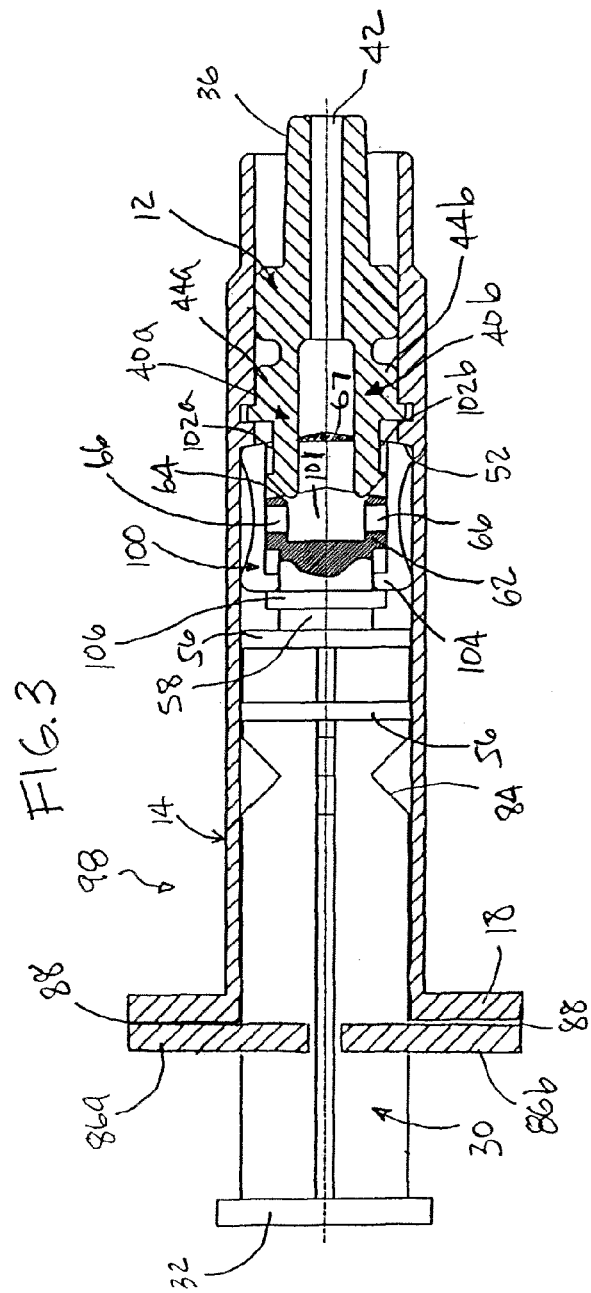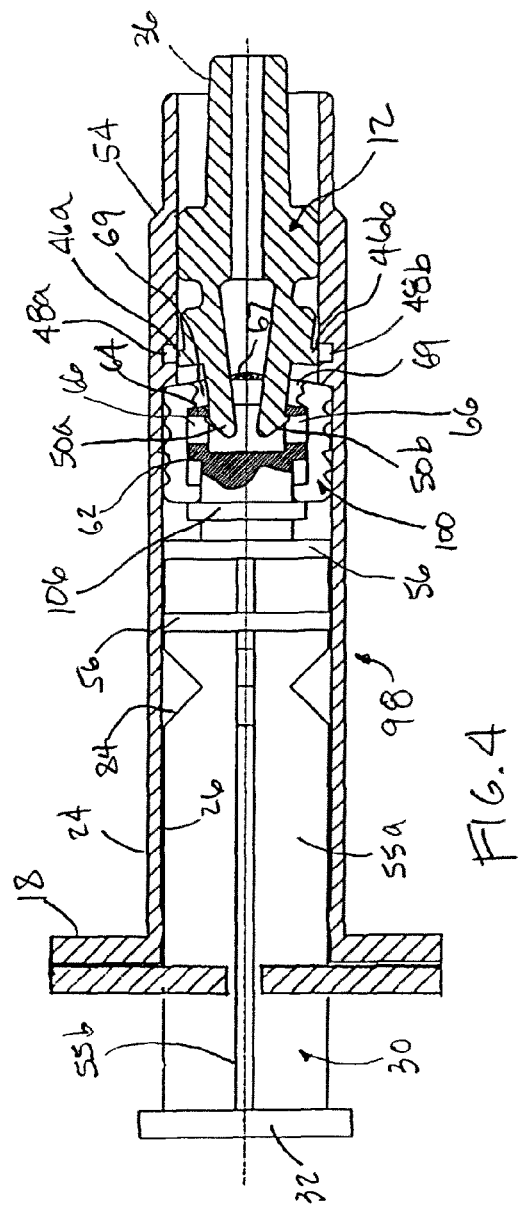

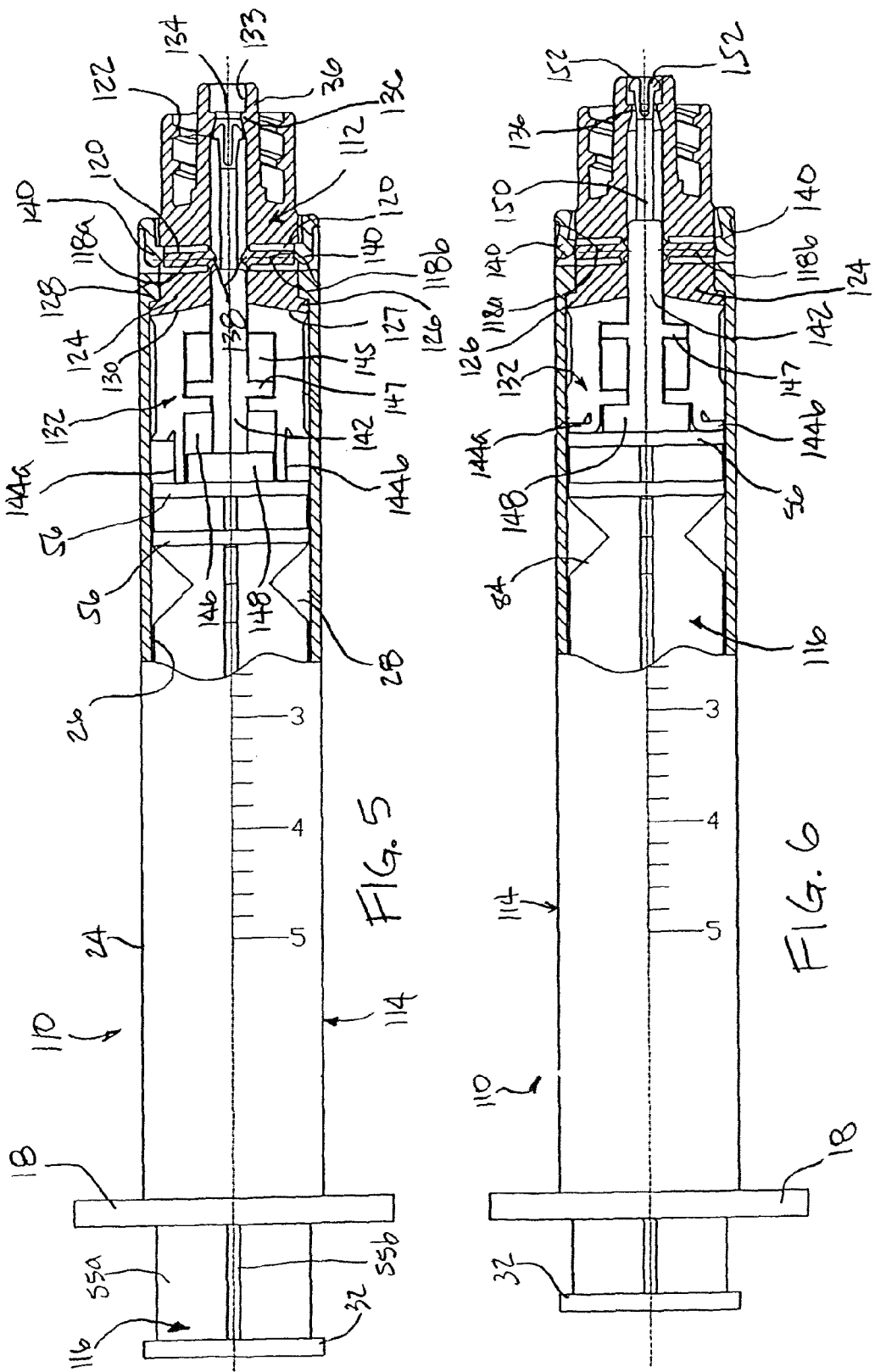

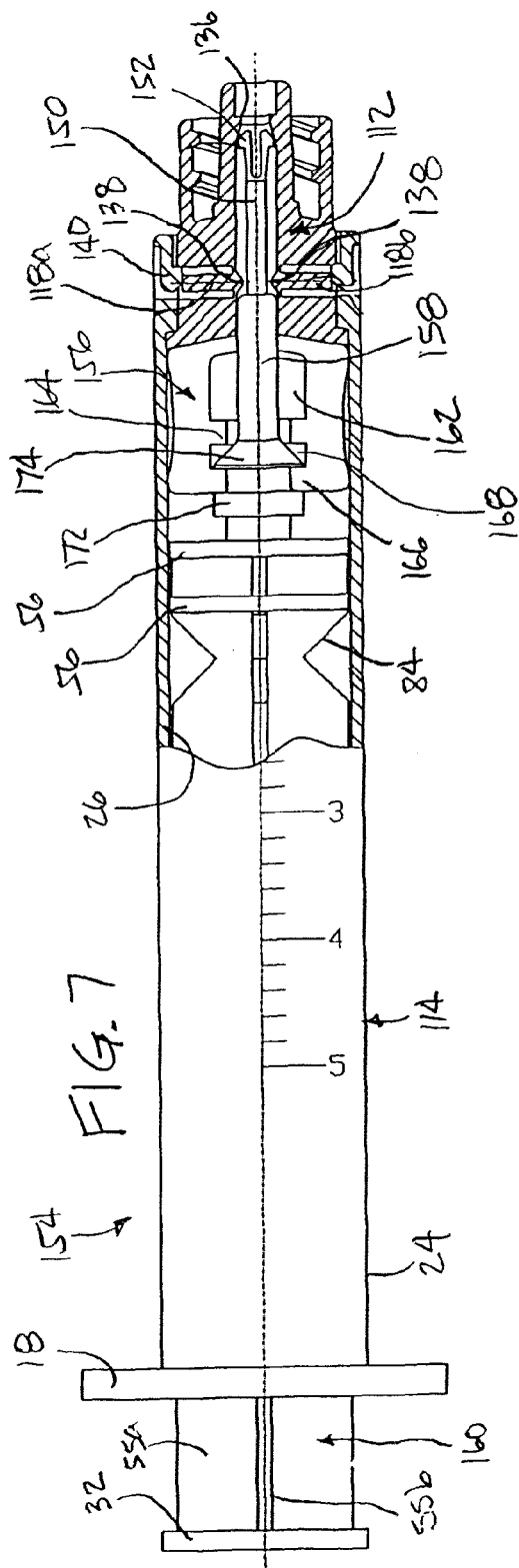

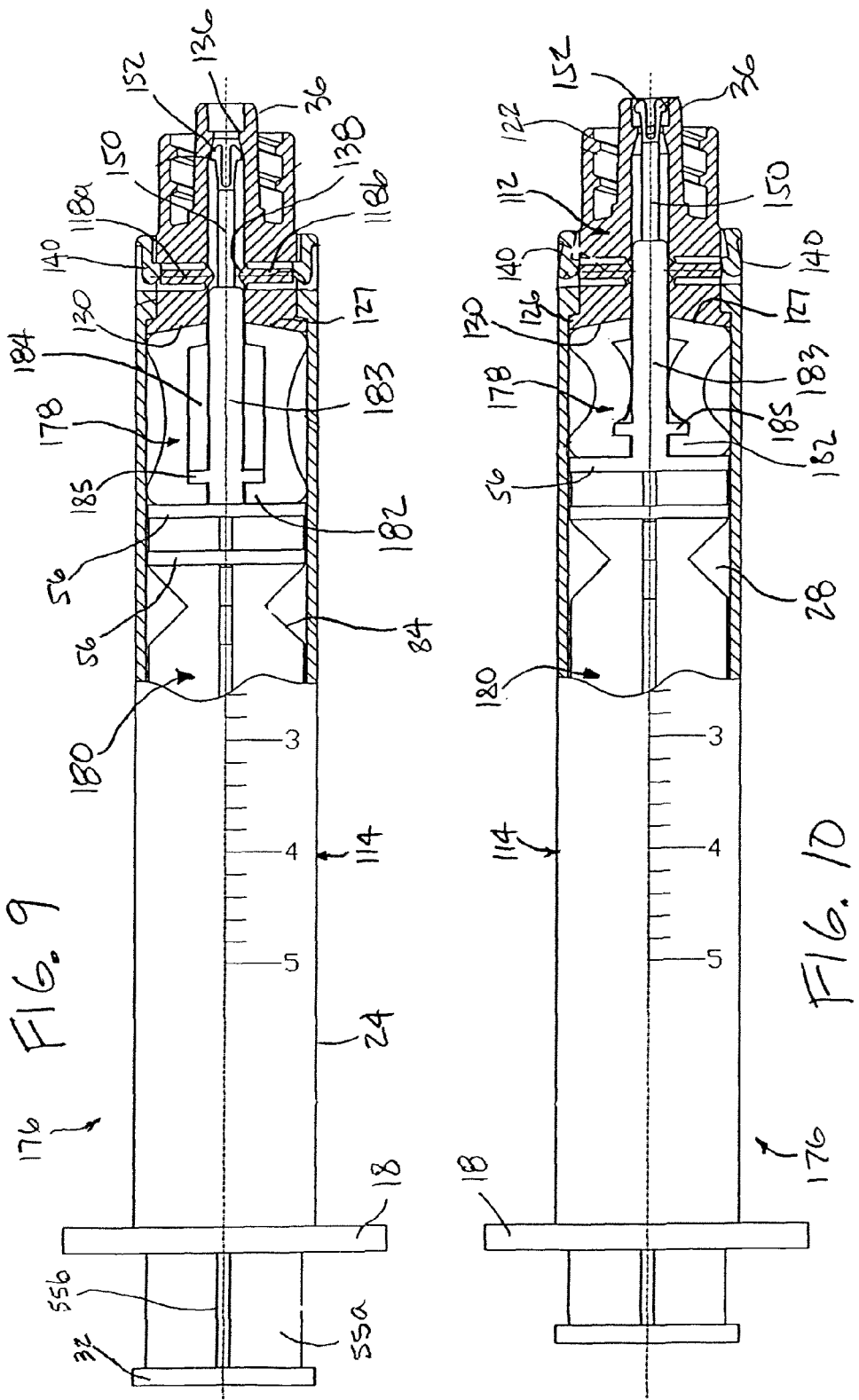

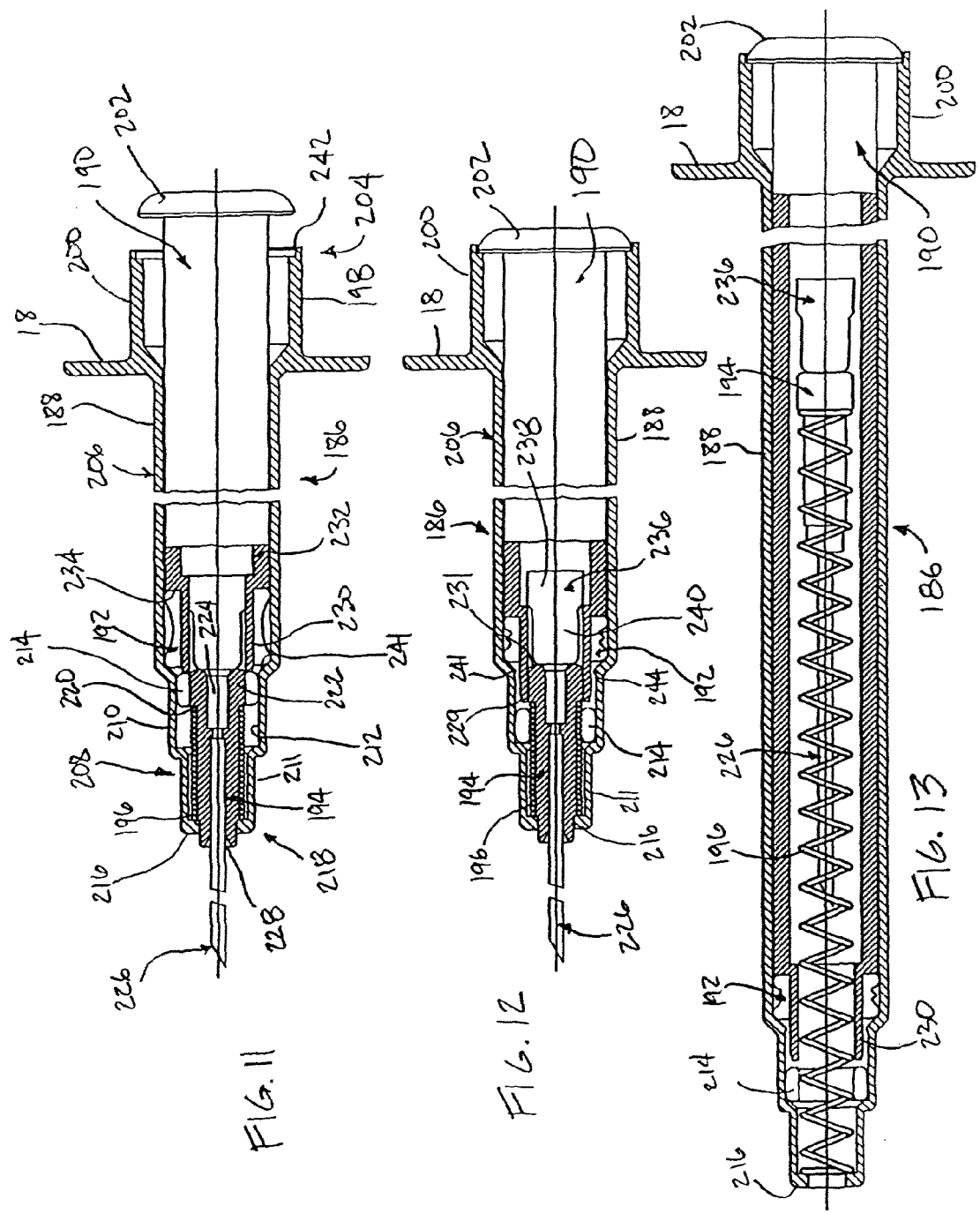

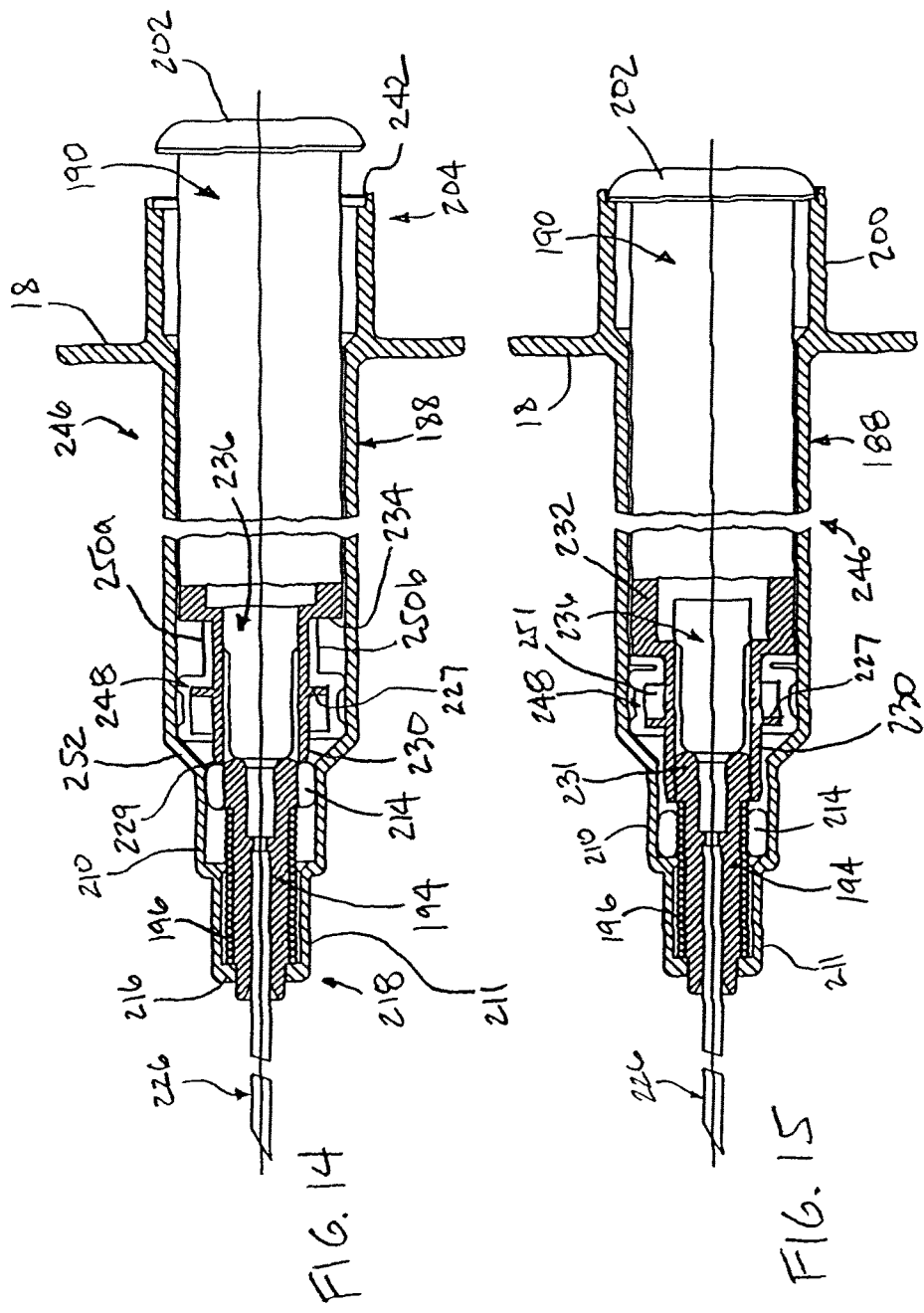

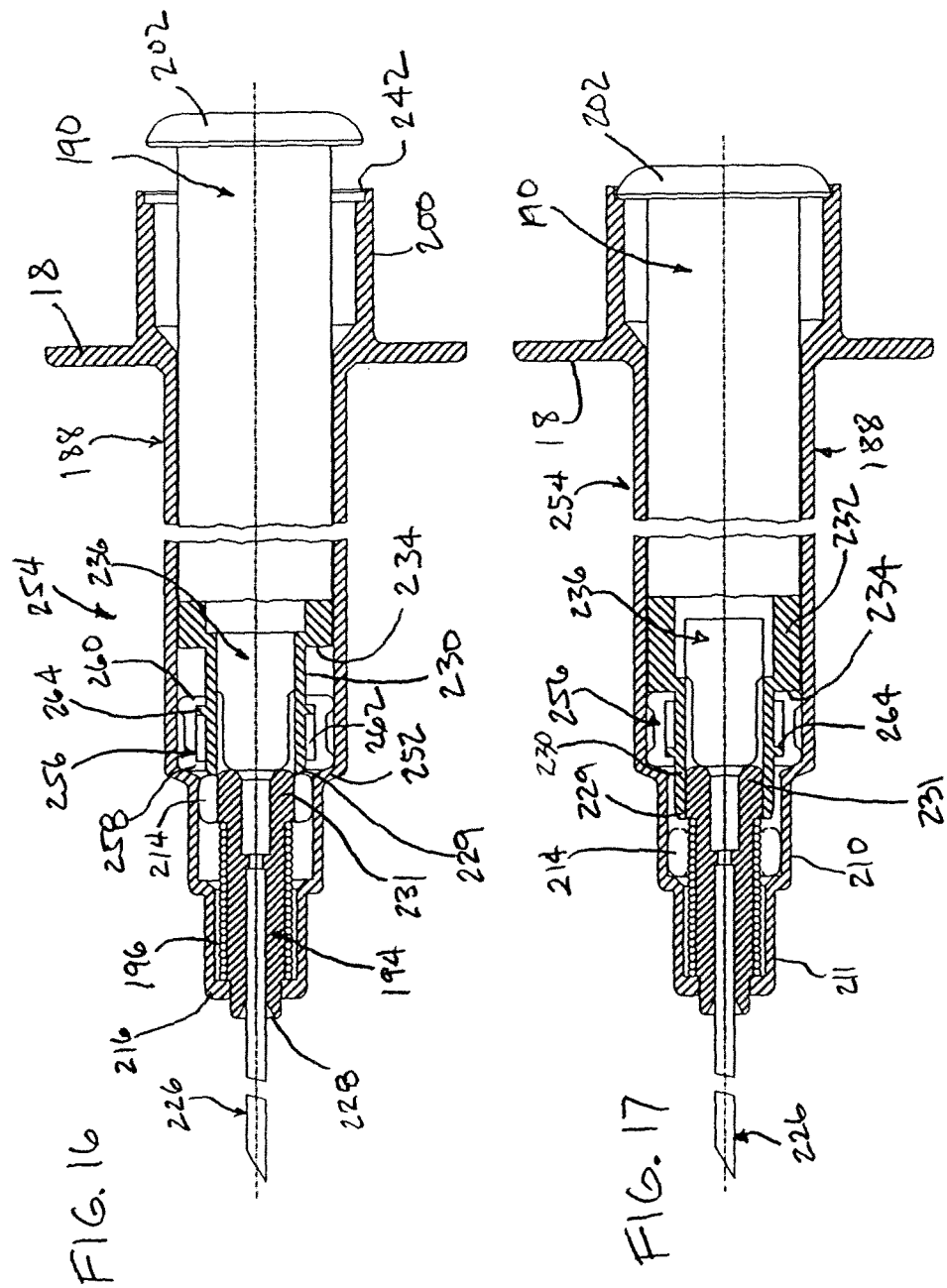

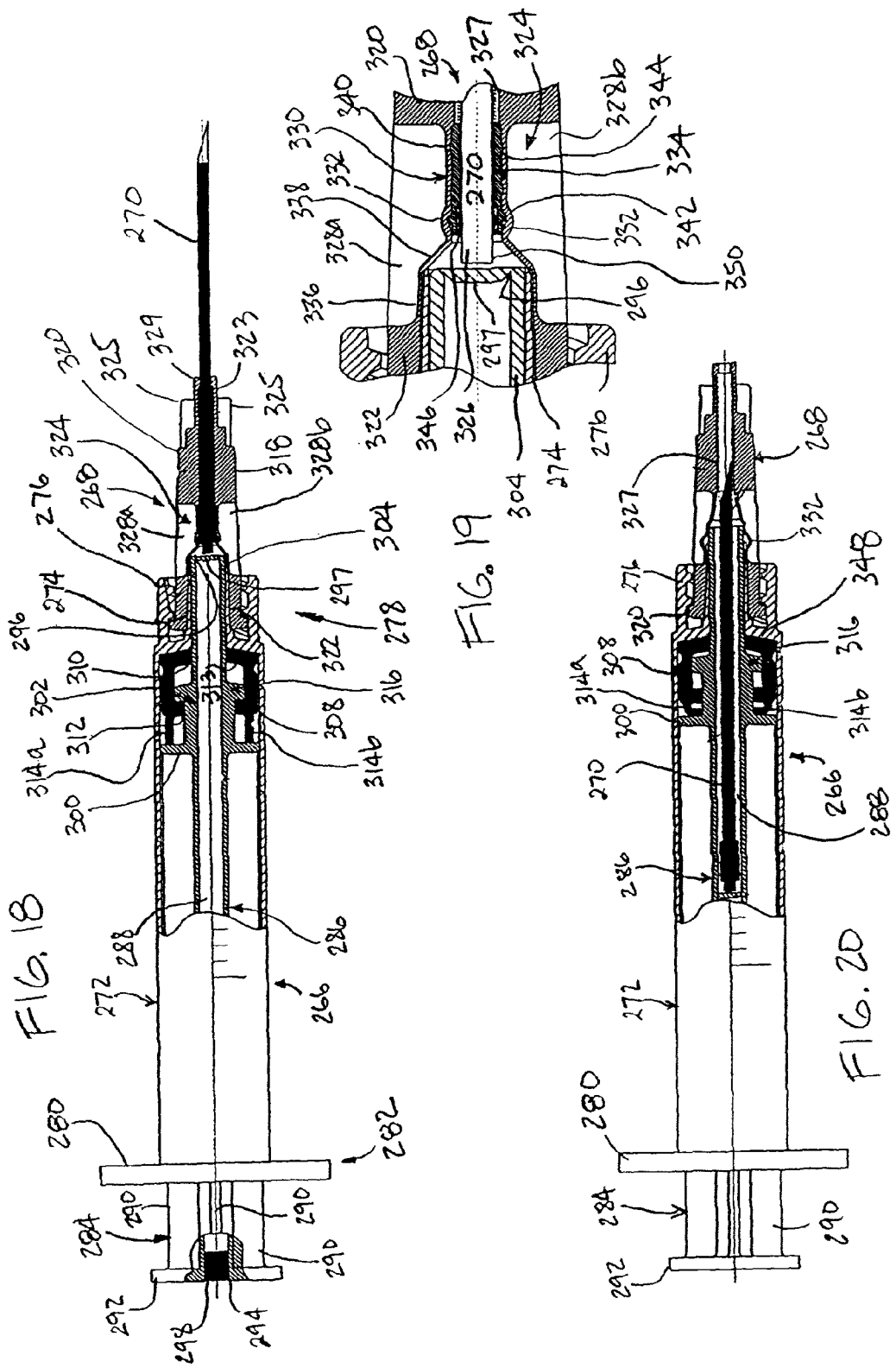

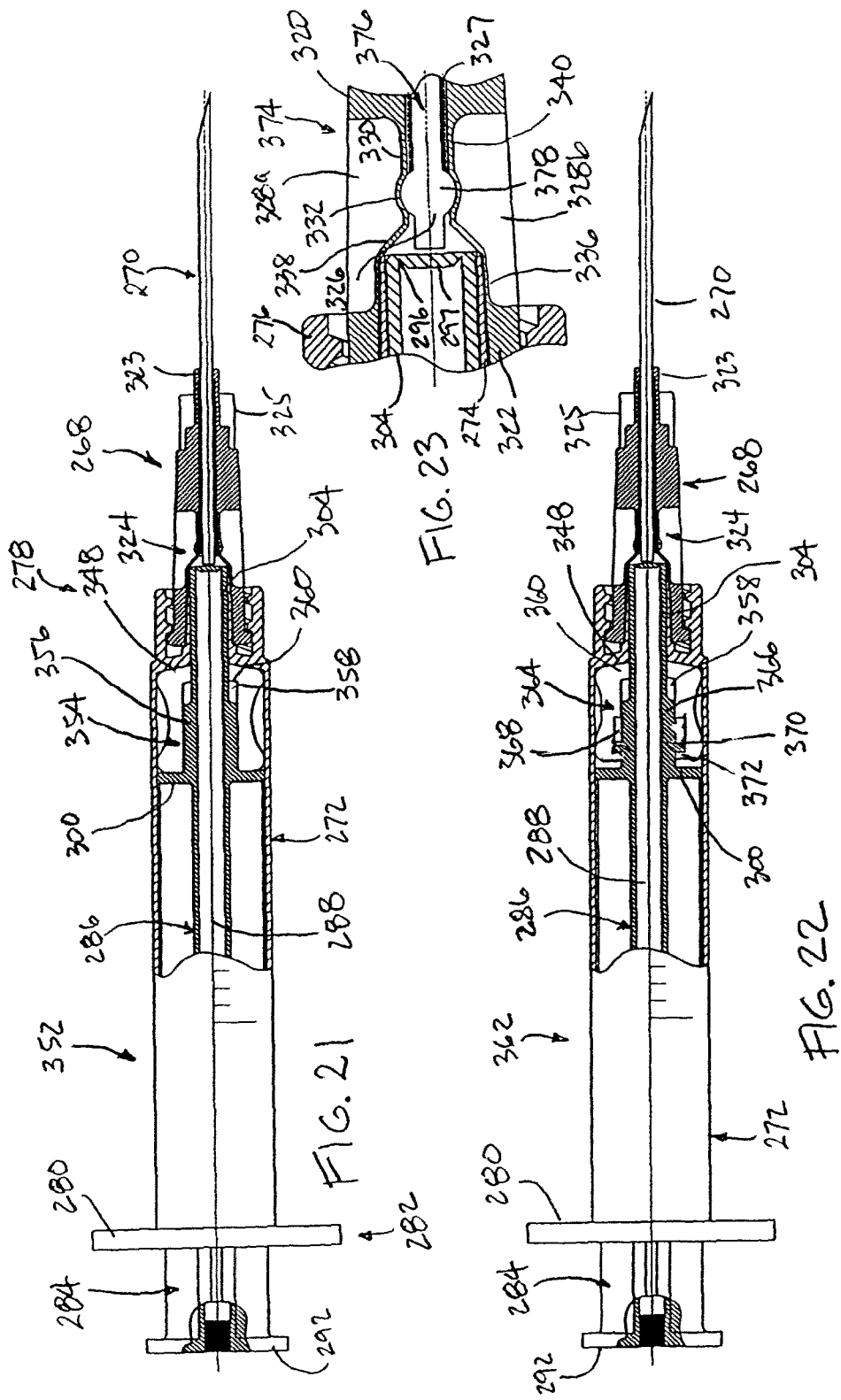

SAFETY SYRINGES

CROSS-REFERENCE TO RELATED APPLICATIONS

This application is a divisional of U.S. patent application Ser. No. 10/769,067, filed on Jan. 30, 2004 ("the '067 application"), now U.S. Pat. No. 7,530,966, the contents of which are incorporated herein by reference. The '067 application claims priority to German Utility Model DE 20 303 231 U1, filed on Feb. 27, 2003, the contents of which are also incorporated herein by reference.

BACKGROUND

Safety syringes for minimizing accidental contact with users are generally discussed herein with particular discussions extended to safety syringes having manual and automatic retractable carriages.

DESCRIPTION OF RELATED ART

Syringes are used for injecting fluids and for withdrawing fluids from fluid carrying sources. In an effort to reduce the transfer of communicable diseases, safety features were added to commercially available syringes to minimize accidental contact or sticking with used needle tips.

Principally among these safety features are tip protectors and syringes with retractable carriages. Broadly speaking, in the tip protector technology, a protective element is mounted over a needle and configured to cover the needle tip of the needle subsequent to an injection to block the needle tip. The protective element may be activated manually to cover the needle tip or automatically by way of releasing a spring to then push the protective element over the needle tip.

In the retractable carriage technology, the syringe is fitted with a movable carriage at a distal end of the syringe barrel. The carriage may incorporate a fixed needle or a Luer tip for mounting a needle hub with a needle. After an injection, the carriage can be retracted into the interior cavity of the syringe barrel along with the needle to prevent needle stick. More particularly, following an injection, the carriage is typically engaged by a plunger and retracted into the interior cavity of the barrel by pulling onto the plunger in the opposite or proximal direction. Alternatively, the carriage is disengaged from the barrel by the plunger and a spring automatically retracts the carriage into the interior cavity of the barrel.

Although the prior art safety features for syringes are useful, the safety syringes described elsewhere herein are better alternatives. Among other things, the prior art safety devices have shortcomings in that the air cannot be completely expelled from the syringe barrel prior to aspirating fluid without triggering the safety mechanism by the plunger. This premature triggering, when attempting to fill the device, makes the prior art syringe ineffective and frustrates the health care worker trying to use it.

SUMMARY

One embodiment of the present safety syringes comprises a barrel including a gripping flange at a proximal end, an end wall at a distal end defining an opening, an internal shoulder at a location spaced from the end wall, and a sidewall structure comprising an exterior surface and an interior surface defining an interior cavity. The syringe further comprises a plunger including a tubular body having an interior cavity disposed in the interior cavity of the barrel, a push flange at a proximal end, and a plunger tip holder including a push end. The syringe further comprises an elastomeric plunger tip mounted on the plunger tip holder. The plunger tip is shaped substantially as a smoothly tapered cylinder having a constant inner diameter between its proximal end and its distal end, and has relatively greater wall thickness at the proximal and distal ends and relatively lesser wall thickness at locations in between the proximal and distal ends. The proximal end abuts a shoulder on the tubular body. The syringe further comprises a carriage including an elongated body having a spring located thereon, a base extending from the elongated body, a shoulder positioned between the elongated body and the base, and a passage receiving a needle. The spring is compressed by the end wall of the barrel and the shoulder on the carriage and the carriage is removably secured to the barrel by a resilient holding tire wedged between the base of the carriage and the interior surface of the barrel. The plunger comprises three plunger positions including a first plunger position in which the plunger tip is spaced apart from the carriage, a second plunger position in which the plunger tip simultaneously contacts the shoulder on the plunger and the internal shoulder on the barrel while the holding tire is positioned on the base of the carriage, and a third plunger position in which the push end on the plunger has pushed the holding tire distally off of the base of the carriage.

Another embodiment of the present safety syringes comprises a barrel including a gripping flange at a proximal end, an end wall at a distal end defining an opening, an internal shoulder at a location spaced from the end wall, and a sidewall structure comprising an exterior surface and an interior surface defining an interior cavity. The syringe further comprises a plunger including a tubular body having an interior cavity disposed in the interior cavity of the barrel, a push flange at a proximal end, and a plunger tip holder. The plunger tip holder includes a push end, a shoulder defining a boundary between a relatively greater diameter portion and relatively lesser diameter portion, and a radially outward projection located distal of the shoulder. The syringe further comprises an elastomeric plunger tip mounted on the relatively lesser diameter portion of the plunger tip holder. The plunger tip includes a proximal annular ring and a distal annular ring. The proximal and distal annular rings have the same internal diameter. The syringe further comprises a carriage including an elongated body having a spring located thereon, a base extending from the elongated body, a shoulder positioned between the elongated body and the base, and a passage receiving a needle. The spring is compressed by the end wall of the barrel and the shoulder on the carriage and the carriage is removably secured to the barrel by a resilient holding tire wedged between the base of the carriage and the interior surface of the barrel. The plunger comprises three plunger positions including a first plunger position in which the plunger tip is spaced apart from the carriage, a second plunger position in which the plunger tip contacts the shoulder on the barrel and the radially outward projection on the plunger contacts the proximal annular ring on the plunger tip while the holding tire is positioned on the base of the carriage, and a third plunger position in which the push end on the plunger has pushed the holding tire distally off of the base of the carriage, the radially outward projection on the plunger contacts the distal annular ring on the plunger tip, and the shoulder on the plunger contacts the proximal annular ring on the plunger tip.

BRIEF DESCRIPTION OF THE DRAWINGS

These and other features and advantages of the present invention will become appreciated as the same become better understood with reference to the specification, claims and appended drawings wherein:

FIG. 1 is a semi-schematic cross-sectional view of a syringe with a manual retractable carriage provided in accordance with aspects of the present invention;

FIG. 2 is a semi-schematic cross-sectional view of the syringe of FIG. 1 with the carriage engaged by a plunger for retracting into the barrel of the syringe;

FIG. 2a is a semi-schematic cross-sectional view of an alternative plunger tip provided in accordance with aspects of the present invention;

FIG. 2b is a semi-schematic exemplary plan view of two alignment plates incorporated by the syringe of FIG. 1;

FIG. 3 is a semi-schematic cross-sectional view of an alternative syringe with a manual retractable carriage provided in accordance with aspects of the present invention;

FIG. 4 is a semi-schematic cross-sectional view of the syringe of FIG. 3 with the carriage engaged by a plunger for retracting into the barrel of the syringe;

FIG. 5 is a semi-schematic cross-sectional view of another alternative syringe with a manual retractable carriage provided in accordance with aspects of the present invention;

FIG. 6 is a semi-schematic cross-sectional view of the syringe of FIG. 5 with the carriage engaged by a plunger for retracting into the barrel of the syringe;

FIG. 7 is a semi-schematic cross-sectional view of yet another alternative syringe with a manual retractable carriage provided in accordance with aspects of the present invention;

FIG. 8 is a semi-schematic cross-sectional view of the syringe of FIG. 7 with the carriage engaged by a plunger for retracting into the barrel of the syringe;

FIG. 9 is a semi-schematic cross-sectional view of yet another alternative syringe with a manual retractable carriage provided in accordance with aspects of the present invention;

FIG. 10 is a semi-schematic cross-sectional view of the syringe of FIG. 9 with the carriage engaged by a plunger for retracting into the barrel of the syringe;

FIG. 11 is a semi-schematic cross-sectional view of a syringe with a spring loaded carriage provided in accordance with aspects of the present invention;

FIG. 12 is a semi-schematic cross-sectional view of the syringe of FIG. 11 with the carriage disengaged and ready for retraction;

FIG. 13 is a semi-schematic cross-sectional view of the syringe of FIG. 11 with the carriage retracted inside the barrel;

FIG. 14 is a semi-schematic cross-sectional view of an alternative syringe with a spring loaded carriage provided in accordance with aspects of the present invention;

FIG. 15 is a semi-schematic cross-section view of the syringe of FIG. 14 with the carriage disengaged and ready for retraction;

FIG. 16 is a semi-schematic cross-sectional view of another alternative syringe with a spring loaded carriage provided in accordance with aspects of the present invention;

FIG. 17 is a semi-schematic cross-sectional view of the syringe of FIG. 16 with the carriage disengaged and ready for retraction;

FIG. 18 is a semi-schematic partial cross-sectional view of a syringe with a needle hub having a spring loaded retractable needle provided in accordance with aspects of the present invention;

FIG. 19 is a semi-schematic partial enlarged view of the needle hub of FIG. 18;

FIG. 20 is a semi-schematic partial cross-sectional view of the syringe of FIG. 18 with the needle retracted partially into the barrel;

FIG. 21 is a semi-schematic partial cross-sectional view of an alternative syringe with a needle hub having a spring loaded retractable needle provided in accordance with aspects of the present invention;

FIG. 22 is a semi-schematic partial cross-sectional view of another alternative syringe with a needle hub having a spring loaded retractable needle provided in accordance with aspects of the present invention; and FIG. 23 is a semi-schematic partial enlarged view of an alternative needle hub having a spring loaded retractable needle provided in accordance with aspects of the present invention.

DETAILED DESCRIPTION

Figure 14A:
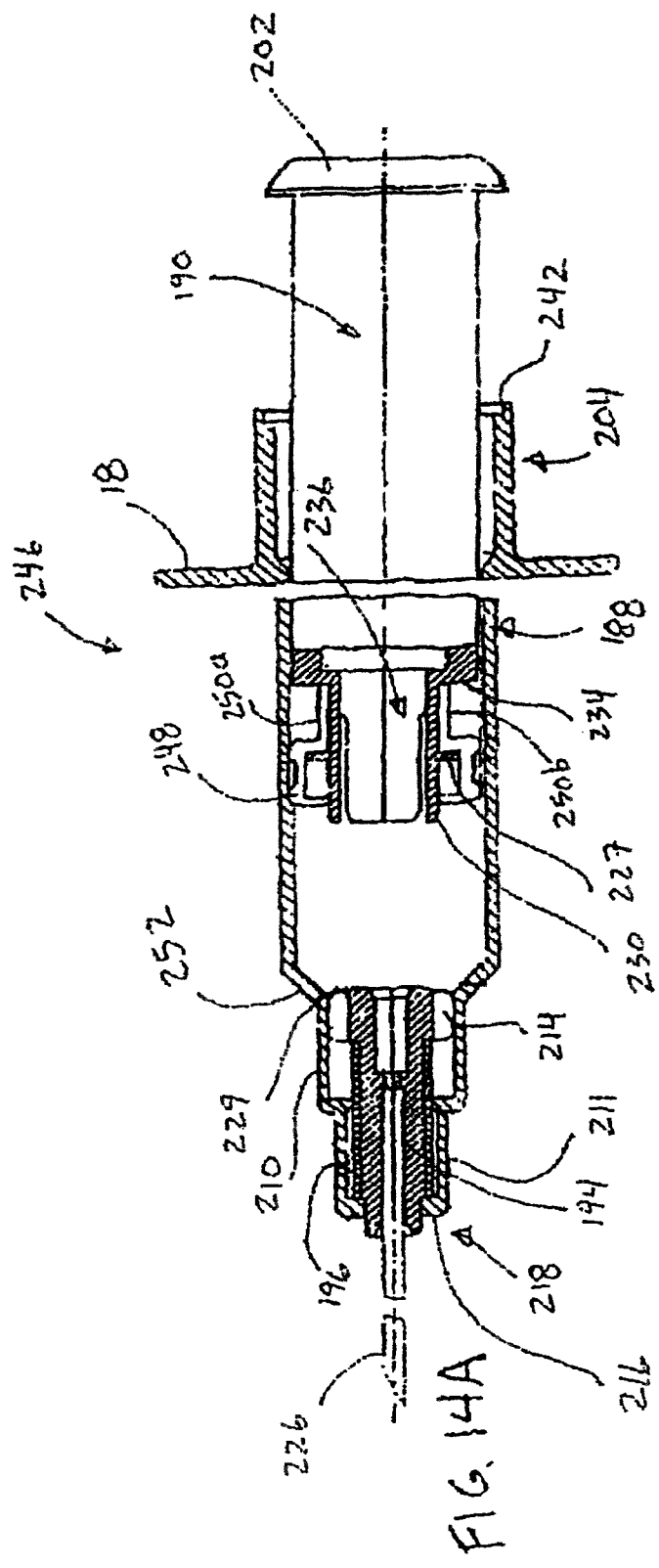
FIG. 14A is a semi-schematic cross-sectional view of the syringe of FIG. 14 in a plunger first position.

The detailed description set forth below in connection with the appended drawings is intended as a description of the presently preferred embodiments of safety syringes provided in accordance with practice of the present invention and is not intended to represent the only forms in which the present invention may be constructed or utilized. The description sets forth the features and the steps for constructing and using the safety syringes of the present invention in connection with the illustrated embodiments. It is to be understood, however, that the same or equivalent functions and structures may be accomplished by different embodiments that are also intended to be encompassed within the spirit and scope of the invention. Also, as denoted elsewhere herein, like element numbers are intended to indicate like or similar elements or features.

Referring now to FIG. 1, an exemplary syringe 10 with a retractable carriage 12 provided in accordance with aspects of the present invention is shown. In one exemplary embodiment, the syringe 10, which may be of any standard sizes such as 5 ml or 10 ml, comprises a barrel 14, a proximal end 16 with a grip flange 18, and a distal end 20 with an opening 22 for receiving a standard needle hub having a needle attached thereto (not shown).

The barrel 14 defines a wall surface which has an exterior surface 24 and an interior surface 26, which defines an interior cavity 28. Positioned in the interior cavity 28 are the plunger 30, which has a push flange 32 on one end and a plunger tip or seal 34 on another end, and the carriage 12. In one exemplary embodiment, the carriage 12 comprises a male Luer tip 36, a sealing ring 38, and a pair of proximally extending arms 40a, 40b. The sealing ring 38 is configured to seal against the interior surface 26 of the barrel 14 and in combination with a portion of the interior surface 26 of the barrel 14 defines a volume enclosure, which is variable depending on the position of the plunger 30 and plunger tip 34 relative to the barrel. A lumen 42 is defined through the axial center of the carriage 12 for fluid communication between the interior cavity 28 of the syringe and exteriorly of the barrel 14 variable volume enclosure. The plunger tip 34 is dynamically sealed against the interior surface 26 of the barrier by well known methods.

The proximally extending arms 40a, 40b are cantilevered to the base of the sealing ring 38 by a pair of integrally molded bridges 42a, 42b (FIG. 2). The cantilevered configuration permit the arms 40a, 40b to flex radially inwardly in the direction of the longitudinal axis defined by the lengthwise central axis of the barrel for reasons discussed further below. Just proximal of the bridges 42a, 42b are the raised ridges 44a, 44b and the male detents 46a, 46b, which matingly engage with the female detents 48a, 48b formed in the interior surface 26 of the barrel 14 when the carriage 12 is in the ready to use position. Two actuated ramps 50a, 50b are positioned further proximal of the male detents 46a, 46b. In one exemplary embodiment, the actuated ramps 50*a*, 50*b* incorporate diagonal faces for imparting a pair of component forces to the arms 40*a*, 40*b* when pushed by the plunger 30 to flex the arms 40*a*, 40*b* radially inwardly, as further discussed below. The actuated ramps 50*a*, 50*b* terminate in a hook-like configuration for engaging with the shroud 62 (FIG. 1). The barrel 14, plunger 30, carriage 12, and plunger tip 34 may be made from known materials currently used in the art.

In one exemplary embodiment, the barrel 14 comprises two tapered sections. A first tapered section 52 is formed in the interior cavity 28 of the barrel and acts as a shoulder to stop the distal or forward advancement of the plunger tip 34. The second tapered section 54 is formed on the exterior surface 24 of the barrel 14 for aesthetic appeal that may otherwise be eliminated. Alternatively, the tapered sections 52, 54 may be squared, or may incorporate a combination of a squared finish and a tapered finish. The barrel is preferably transparent or semi-transparent and may include indicia such as labeling, markings, or other features for references.

In one exemplary embodiment, the plunger 30 incorporates a pair of elongated plates 55*a*, 55*b* having a plus ("+")-shaped cross-section. One or more push plates 56 may be formed on plunger 30 for reinforcement. A distally projecting post or tip holder 58 is positioned distal of the one or more push plates 56 for positioning the plunger tip 34 thereon. A plunger disc 60 is formed on the distally projecting post 58 and is preferably spaced from the most distal push plate 56 by a gap, which should be of sufficient width for accommodating a portion of the plunger tip 34, as further discussed below. A generally cylindrical shroud 62 is positioned distal of the plunger disc 60 having a pusher end 64 (FIG. 2) and a pair of receiving slots 66. In one exemplary embodiment, the pusher end 64 and the plunger disc 60 each comprises a tapered surface for reasons further discussed below. The receiving slots 66 should have a dimension sufficient to receive the hook-like ends of the actuated ramps 50*a*, 50*b*.

The shroud 62 comprises a distal end surface 67 having a pair of openings 69 for receiving the proximally extending arms 40*a*, 40*b* of the carriage 12. The plunger tip 34 comprises a bore 68 for receiving the shroud 62. In one exemplary embodiment, the bore 68 of the plunger tip comprises a first diameter section 70, a second diameter section 72, and a third diameter section 74 (FIG. 2). However, the internal bore 68 can have a same diameter by modifying the dimensions of the post 58, shroud 62, and/or carriage 12. An inwardly extending ring 76 is formed on the proximal end of the plunger tip 34 and sized to form a size-on-size friction fit with the distally projecting post 58 of the plunger 30. A second inwardly extending ring 78 spaced from the first inwardly extending ring 76 is positioned at the transition between the second diameter section 72 and the third diameter section 74 of the plunger tip. The space or gap 80 between the first 76 and second 78 inwardly extending rings functions as an activation gap and is configured to receive the plunger disc 60 when the plunger 30 is advanced distally to activate or retract the carriage 12, as further discussed below.

In an alternative plunger tip 34' embodiment (FIG. 2*b*), the second inwardly extending ring 78 may be omitted and the proximal end 61 of shroud 62' extended or moved further proximal to be adjacent the distal side of extending ring 76'. This eliminates the need for a gap 80 and simplifies the form of plunger tip 34'. The alternative plunger tip 34' otherwise functions the same as the plunger tip 34 of FIGS. 1 and 2.

To use the syringe 10, a commercially available needle attached to a needle hub (not shown) is first mounted onto the Luer tip 36. Because the syringe 10 has a Luer tip 36 and not a permanently attached needle on the carriage 12, different needle sizes may be mounted onto the Luer tip for aspirating, withdrawing a sample, or performing an injection. Preferably, if the syringe is used to withdraw a sample, the needle with the needle hub should include a tip protector or clip for covering the needle tip.

With the barrel 14 filled with a medicinal fluid, which can be any number of fluids, to a desired volume and the needle injected into a subject, the plunger 30 is advanced distally with a distally directed force $F_D$ in the direction of the needle to discharge the fluid. The injection is completed when the plunger tip 34 contacts the shoulder or first tapered section 52 of the barrel 14. At this point, preferably the needle is withdrawn from the subject by pulling on the plunger 30 via the push flange 32 while pushing the barrel 14 distally against the patient's skin. The needle and carriage 12 retraction into the barrel are simultaneously accomplished as described in detail below. Alternatively, the needle can be withdrawn from the patient prior to retracting the needle into the barrel 14.

To retract the carriage 12 with the needle still mounted thereto, the plunger 30 is further advanced distally with an activated force $F_A$ sufficient to bend the proximally extending arms 40*a*, 40*b* inwardly at the bridges 42*a*, 42*b*, which act as fulcrum points. In one exemplary embodiment, the activated force $F_A$ is greater than the distally advancing force $F_D$ so that a user in using the syringe 10 can feel a clear delineation between injecting a fluid and withdrawing the carriage 12.

The bending of the arms 40*a*, 40*b* occur when the pusher end 64 of the shroud 62, which preferably comprises a tapered face, contacts the actuated ramps 50*a*, 50*b* of the arms 40*a*, 40*b* and impart a pair of component forces. The arms 40*a*, 40*b* bend radially inwardly and the male detents 46*a*, 46*b* separate from the female detents 48*a*, 48*b* as the plunger 30 advances distally under an actuated force $F_A$. The arms continue to bend as until the hook-like ends of the actuated ramps 50*a*, 50*b* latch with the receiving slots 66*a*, 66*b* located in of the shroud 62. When the activated force $F_A$ is no longer applied, the arms 40*a*, 40*b*, due to their resiliency, snap radially outwardly a small radial distance to securely engage with the slots 66*a*, 66*b* (FIG. 2).

During the activation step, the plunger disc 60 pushes against the inwardly extending ring 76 of the plunger tip 34 until the ring 76, due to its resiliency, pops over the disc 60 so that the disc can then move into the activated space 80. As readily apparent, subsequent to the plunger tip 34 abutting the shoulder 52 of the barrel and stop moving, the plunger 30 may still move distally relative to the plunger tip to disengage the carriage 12 from the barrel 14. Unrestrained, the carriage 12 and needle (not shown) can then be retracted into the interior cavity 28 of the barrel 14 by grasping and pulling on the push flange 32 proximally to retract the needle into the barrel 14.

To prevent retracting the carriage 12 too far into the barrel 14 and possibly dislodge the carriage 12 from the barrel 14 and to also prevent the needle from protruding back out the distal end 20 of the barrel, in one exemplary embodiment, a stop ring 82 (FIG. 2), which may comprise an annular projection on the interior surface 26 of the barrel near the grip flange 18, may be incorporated to hold the plunger 30 in the completely retracted position. The plunger 30 may include a notch 84 along each edge of the elongated plates 55*a*, 55*b* to provide a breaking point for breaking off the plunger and avoiding accidentally pushing the needle distally into an unprotected position. Once the carriage 12 is retracted into the barrel and the plunger 30 broken off, the syringe may be safely disposed of per standard protocols.

For aligning the hooks on the actuated ramps 50*a*, 50*b* of the carriage 12 with the receiving slots 66*a*, 66*b* located on the shroud 62 of the plunger 30, alignment plates 86*a*, 86*b* may be incorporated at the proximal end 16 of the barrel 14. The alignment plates 86a, 86b may be integrally molded with the push flange 18 via living hinges 88 and then glued, welded, or engaged to the push flange 18 by detents. Alternatively, the alignment plates 86a, 86b may be separately attached to the push flange 18 via adhesive, welding, or detents without the living hinges 88.

Referring to FIG. 2a, which is an exemplary plan view of the alignment plates 86a, 86b, each alignment plate 86a or 86b comprises a gripping portion 90 and a semi-circular portion 92 comprising a slot 94 and a part of a slot 96. The two alignment plates 86a, 86b come together at a parting line and the two part slots 96 on each alignment plate makes a whole slot. The two whole slots 94 are sized to receive one rectangular plate 55a of the plunger 30 while the partial slots 96 together receive the other rectangular plate 55b of the plunger 30. Cooperation between the alignment plates 86a, 86b and the rectangular plates 55a, 55b prevents the plunger 30 from angularly rotating and misaligning the hooks on the actuated ramps 50a, 50b with the receiving slots 66a, 66b located on the shroud 62.

Turning now to FIG. 3, an alternative manual retractable syringe 98 provided in accordance with aspects of the present invention is shown. The syringe 98 has features that are similar with features described above for the syringe 10 shown with reference to FIGS. 1-2A with the exception of the plunger tip 100 and the manner in which the plunger tip engages and interacts with the plunger 30. In the present syringe 98 embodiment, the shroud 62 incorporates two openings 102a, 102b at the distal end surface 67 for receiving the proximally extending arms 40a, 40b. The plunger tip 100 comprises a bore 101 having a substantially uniform inside diameter for receiving the shroud 62. An inwardly extending ring 104 is incorporated at the proximal end of the plunger tip 100 and sized to form a size-on-size friction fit with the distally projecting post 58 of the plunger 30. In the ready to use configuration of FIG. 3, the inwardly extending ring 104 abuts the plunger disc 106 located on the post 58 of the plunger 30, which in the present embodiment does not incorporate a tapered face. A shroud 62 comprising a pair of receiving slots 66 and pusher end 64 is disposed inside the bore 101 of the plunger tip 100 for engaging with the hooks on the carriage 12 and retracting the same into the barrel 14.

The syringe 98 may be used and the carriage 12 may be retracted into the barrel 14 in the same manner as described above with reference to the syringe 10 of FIGS. 1 and 2. More particularly, following an injection, the distal end of the plunger tip 100 abuts the barrel shoulder 52 and the proximally extending arms 40a, 40b of the carriage 12 project into the openings 69 of the distal end surface 67 of the shroud 62. To retract the carriage 12, an activated force $F_A$ is then applied on the plunger 30 to further advance the plunger distally relative to the distal end of the plunger tip 100. This activated force $F_A$ causes the pusher end 64 of the shroud 62 to exert a pair of component forces to the actuated ramps 50a, 50b, which then bends the proximally extending arms 40a, 40b radially inwardly. At the same time, the plunger disc 106 pushes against the inwardly extending ring 104 and compresses the plunger tip 100 (FIG. 4).

The carriage 12 may be withdrawn proximally into the barrel 14 when the male detents 46a, 46b disengage from the female detents 48a, 48b and the hooks on the end of the arms 40a, 40b engage the receiving slots 66 located on the shroud 62. During the retraction procedure, the plunger tip 100 will expand in the distal direction until it touches or reaches near the proximal edge 108 of the side ridges 44a, 44b of the carriage 12.

FIG. 5 shows another alternative retractable syringe 110 provided in accordance with aspects of the present invention. The syringe 110 is similar to the syringes of FIGS. 1-4 with the exception the carriage 112 and the manner in which it engages the barrel 114 and is retracted by the plunger 116. In one exemplary embodiment, the carriage 112 incorporates a pair of actuated pistons 118a, 118b formed in two wells 120 located on the carriage. The carriage 112 further comprises a female lock 122 around a Luer tip 36, and a hub. 124 proximal of the actuated pistons 11a, 118b. The hub 124 incorporates a flange 126 for abutting against the shoulder 128 located on the barrel 114 to axially align the carriage 112 relative to the barrel 114 during engagement of the carriage 112 to the barrel 114. The hub 124 includes a proximal surface 127 having a configuration to accommodate the contour of the distal end surface 130 of the plunger tip 132.

The carriage 112 comprises a bore 133 which defines a lumen 134 for fluid communication between the variable interior cavity 28 of the barrel 114 and the needle (not shown) which may be mounted to the syringe by the way of mounting a needle hub to the Luer tip 36. In one exemplary embodiment, the bore 133 incorporates two inward projections for interacting with the plunger 116. The first projection 136 is located near the opening of the Luer tip 36 and has a tapered or sloped surface on a proximal side. On the edge opposite the sloped surface, the first projection 136 preferably comprises a square finish, for reasons further discussed below. The second projection 138 is formed subjacent the two actuated pistons 118a, 118b. To fixedly secure the carriage 112 to the barrel 114, the barrel incorporates a pair of hinged hooks 140 at the distal end of the barrel. The hinge hooks 140 engage an edge of the wells 120 located on the carriage 112 to lock the carriage to the barrel. The hinge hooks 140 can be integrally molded on the carriage 112.

In one exemplary embodiment, the plunger tip 132 incorporates a bore for receiving the extension pin or distally projected post 142 of the plunger 116, an internal space or cavity 145, and a pair of extension legs 144a, 144b for setting a gap between certain parts of the plunger 116 and of the plunger tip 132. A gap or a space 146 located in between the extension legs 144a, 144b are configured to receive a drum 148 located at the base of the extension pin 142. The gap or space 146 should have sufficient depth to receive the drum 148 and not delimit or restrict the hooks on the plunger 116 from grabbing the first projection 136 located in the Luer tip 36, as further discussed below. The plunger 116 also comprises a flange 147 set in the internal space 145 of plunger tip 132, and in one exemplary embodiment, comprises a tapered face on its distal side to facilitate assembly over the tip holder. Flange 147 secures plunger tip 132 to the plunger 116 during aspiration of a fluid. The internal space 145 should be sufficiently long to allow the flange 147 to move from a proximal end within the internal space 145 to a distal end during activation so as not to delimit or hinder the hooks 152 from grabbing first projection 136.

A hooking rod 150 comprising a pair of hooks 152 (FIG. 6) extends from the distal end of the extension pin 142 for hooking engagement with the first projection 136 located in the bore of the Luer tip 36. The hooks 152 are configured to deflect when moved distally past a reduced diameter created in the bore of the Luer tip by the first projection 136 to grab the square face of the first projection 136 in a detent configuration.

To retract the carriage 112 into the interior cavity 28 of the barrel 114, the plunger 116 is first advanced distally with a distally directed force $F_D$ until the distal end surface 130 of the plunger tip 132 contacts the proximate surface 127 of the hub 124 of the carriage 112. In this position, the distal end of the extension pin 142 should reside just proximal of the second projection 138 located subjacent the actuated pistons 118a, 118b (FIG. 5). As a distally actuated force $F_A$ force is then applied to the plunger 116, the force causes the extension legs 144a, 144b to bend outwardly, which then moves the extension pin 142 past the second projection 138 to push the actuated pistons 118a, 118b radially outwardly. Concurrently therewith, the actuated pistons 118a, 118b push the hinged hooks 140 on the barrel to unlock the hinged hooks 140 from the wells 120. Also at the same time, the hooks 152 on the hooking rod 150 moves distal of the first projection 136 to then grab the projection. When the plunger is moved in the opposite proximal direction, the interaction between the hooks 152 and the first projection retracts the carriage 112 into the barrel 114.

Although alignment plates 86a, 86b are not required to align parts of the plunger 116 to parts of the carriage 112, the plates 86a, 86b may be included to prevent retracting the plunger 116 completely outside of the barrel 114. Alternatively or in addition thereto, a stop ring 82 may be incorporated near the proximal end of the barrel to engage with the proximal most push plate 56 on the plunger 116 to prevent proximal movement of the plunger. The plunger can then be broken off at the notches 84, as previously described.

In another alternative embodiment (not shown), the hooking rod 150 and hooks 152 are eliminated from the end of the extension pin 142 of the syringe of FIG. 5. A second set of actuated pins proximal of the existing actuated pins 118a, 1118b on the carriage 112 are added, which are to be actuated and engaged by a pair of projections or ramps located on the extension pin 142. In this alternative embodiment, the extension pin 142 would actuate the first set of actuated pins 118a, 118b to disengage the carriage 112 from the barrel 114 and the two projections or ramps on the extension pin 142 would latch or engage with the second set of actuated pins to grab the carriage 112. Once the plunger is retracted, the cooperation between the ramps and the second set of activated pins retract the carriage proximally into the barrel. In this embodiment, the diameter of the extension pin proximal of the two projections or ramps (i.e., the base of the extension pin) should have the same diameter as the largest cross-sectional-dimension of the projections or ramps measured at their widest peaks.

FIG. 7 is another alternative retractable syringe 154 provided in accordance with aspects of the present invention. The syringe 154 is substantially similar to the syringe 110 described above with reference to FIGS. 5 and 6 with the exception of the plunger tip 156 and extension pin 158 of the plunger 160, which are different. In the present embodiment, the extension legs 144a, 144b of the plunger tip are eliminated and a bore 162 incorporated with an annular ring 164. A proximal end annular ring 166 spaced apart from the interior annular ring 164 is also incorporated. The two rings define an activation space or gap 168 for accommodating a part of the extension pin 158, as further discussed below.

A pair of plunger discs 172, 174 are incorporated with the base 170 of the extension pin 158 for cooperating with the plunger tip 156. The distal most plunger disc 174 preferably comprises a tapered surface for facilitating advancing the disc past the interior annular ring 164. In one exemplary embodiment, the proximal most plunger disc 172 incorporates a square finish for pushing the proximal annular ring 166 of the plunger tip 156 distally when a distally directed force $F_D$ is applied. However, a slight taper, of less angular offset than the distal most disc 174, may be incorporated by the proximal most disc 172 to facilitate moving the disc 172 past the end annular ring 166 when an activated force $F_A$ is applied (FIG. 8).

To retract the carriage 112 into the interior cavity 28 of the barrel 114, the plunger 160 is first advanced distally with a distally directed force $F_D$ until the distal end surface 130 of the plunger tip 156 contacts the proximal surface 127 of the carriage 112. In this position, the distal end of the extension pin 158 should reside just proximal of the second projection 138 located subjacent the actuated pistons 118a, 118b. As a distally actuated force $F_A$ force is then applied on the plunger 160, the force causes the two plunger discs 172, 174 to move past the two annular rings 166, 164 positioned inside the bore 162 of the plunger tip 156, which concurrently moves the extension pin 158 past the second projection 138 to push the actuated pistons 118a, 118b radially outwardly. Also concurrently therewith, the actuated pistons 118a, 118b push the hinged hooks 140 on the barrel 114 to unlock the hinged hooks 140 from the wells 120. Also at the same time, the hooks 152 on the hooking rod 150 moves distal of the first projection 136 to, then grab the projection. The carriage 112 can now be retracted by pulling on the plunger 160 in the proximal direction. The plunger 160 can then be broken off as previously described.

FIG. 9 shows yet another alternative manual retract syringe 176 provided in accordance with aspects of the present invention. The syringe 176 is substantially similar to the syringes 110, 154 described above with reference to FIGS. 5-8 with the exception of the plunger tip 178 and extension pin 183 of the plunger 180, which are different. More particularly, the extension pin 183 in the present embodiment extends directly from the distal most push plate 56 on the plunger 180 without a base or a drum. In addition, the plunger tip 178 has a single annular end ring 182 without internal annular rings. The extension pin 183 comprises a flange 185 located just distal of the annular end ring 182. The flange 185 is preferably tapered on its distal side to facilitate assembly through the annular end ring 182, but flat on its proximal side to secure the plunger tip 178 on plunger 180 during aspiration of a fluid. The bore or cavity 184 inside the plunger tip 178 should be sufficiently dimension to permit flexing of the plunger tip when compressed by the plunger 180 (FIG. 10).

To retract the carriage 112 into the interior cavity 28 of the barrel 114, the plunger 180 is first advanced distally with a distally directed force $F_D$ until the distal end surface 130 of the plunger tip 178 contacts the proximal surface 127 of the carriage 112. In this position, the distal end of the extension pin 183 should reside just proximal of the second projection 138 located subjacent the actuated pistons 118a, 118b. As a distally actuated force $F_A$ force is then applied on the plunger 180, the force causes the push plate 56 to push against the annular ring 182 of the plunger tip 178 and compresses the plunger tip (FIG. 10). At the same time, the extension pin 183 travels past the second projection 138 to push the actuated pistons 118a, 118b radially outwardly. Also, concurrently therewith, the actuated pistons 118a, 118b push the hinged hooks 140 on the barrel 114 to unlock the hinged hooks 140 from the wells 120 on the carriage 112. Also at the same time, the hooks 152 on the hooking rod 150 moves distal of the first projection 136 to then grab the projection. The carriage 112 can now be retracted by pulling on the plunger in the proximal direction. The plunger can then be broken off at the notches 84, as previously described.

Referring now to FIG. 11, an automatic needle retract syringe 186 provided in accordance with aspects of the present invention is shown. The syringe 186 comprises a syringe barrel 188, a plunger 190 with a plunger tip 192, and a carriage 194 that is spring loaded with a spring 196. The barrel 188 in the present embodiment comprises a gripping section 198 having a grip flange 18 and an enlarged barrel section 200 sized to receive a part of the push flange 202 on the plunger 190. In one exemplary embodiment, the proximal end 204 of the enlarged barrel section 200 comprises a projection or ring for engaging with the perimeter of the push flange 202 when the push flange is pushed up against the barrel 188 to retract the needle (FIGS. 12 and 13), as further discussed below. Alternatively, the diameter of the enlarged barrel section 200 could be sized to form an interference fit with the push flange 202 when the same is moved into the barrel to retract the needle.

Distally of the gripping section 198 is the variable chamber section 206, which stores fluid to be infused or injected and varies in volume depending on the position of the plunger tip 192 relative to the barrel 188. Distal of the variable chamber section 206 is the engagement chamber 208. The engagement chamber 208 comprises a first engagement section 210 comprising an annular interior surface 212 that cooperates with the carriage 194 to compress a holding tire 214, which may be made from any number of elastomeric rubber or of the same elastomer as the plunger tip 192. Distal thereof is the second engagement section 211. The compressed holding tire 214 acts as an anchor to hold the carriage 194 in place or position, which then allows the spring 196 to be compressed between the end wall 216 at the distal end 218 of the barrel 188 and the shoulder 220 located near the base 222 of the carriage 194. As readily apparent, the holding tire 214 should have a compression force exerted on it by the carriage 194 and the barrel 188 sufficient to resists the spring force generated by the compressed spring 196. Additional hold on the holding tire 214 can come from the projection 244 located at the shoulder 241 of the barrel 188.

A passage or lumen 224 is formed at the axial center of the carriage 194 to permit fluid communication between the interior cavity of the barrel 188 and outside the barrel. In one exemplary embodiment, a needle 226 comprising a needle tip is permanently secured to the carriage 194 via gluing the same to the carriage at the glue well 228.

In one exemplary embodiment, the plunger 190 comprises a first tubular section 230 and a second tubular section 232, which defines an exterior shoulder 234 therebetween. The plunger tip 192 is positioned on the exterior surface of the first tubular section 230 and abuts the exterior shoulder 234. Interiorly, a plug 236, which can be made from an elastomer material, is compressed against the interior surface of the second tubular section 232 by its base section 238, which is relatively larger than its frontal projection 240. Prior to activating the spring (FIG. 11), the distal end of the plug 236, the cylindrical end of the first tubular section 230, and the plunger tip 192 are substantially aligned so that they occupy substantially all of the head space of the variable chamber section 206 to substantially discharge all of the fluid within the barrel. To facilitate this goal, the shoulder 241 between the variable chamber section 206 and the engagement chamber 208 can be square to minimize head space. Alternatively, the plunger 192 can be shaped to occupy substantially all of the head space.

To retract the carriage 194, the plunger 190 is first moved distally with a distally directed force $F_D$ until the distal end surface of the plunger tip 192 contacts the shoulder 241 located at the interface between the first engaging section 210 and the variable chamber 206. At this point, the end tip or distal tip 229 of the first tubular section 230 of the plunger 190 contacts the holding tire 214 and the proximal end 231 of the carriage 194 contacts the tip of the plug 236. When an actuated force $F_A$ is then applied on the plunger 190, the first tubular section 230 of the plunger 190 moves over the proximal end of the carriage 194 in a telescoping fashion. At the same time, the plunger tip 192 is compressed by the exterior shoulder 234 on the plunger 190 and the shoulder 241 on the barrel 188.

Further plunger 190 distal movement causes the tip 229 of the tubular portion 230 to move the holding tire 214 distally off the base section 222 of the carriage 194 and the base 238 of the plug 236 away from the interior surface of the first tubular section 230. In one exemplary embodiment, the holding tire 214 and the base 238 of the plug are released simultaneously from their respective seats when the plunger 190 moves distally to retract the carriage 194. In an alternative embodiment, the holding tire 214 moves off of its seat prior to the base 238 of the plug 236 moving off of its seat. Still alternatively, the base 238 of the plug 236 moves off of its seat prior to the holding tire 214 moving off of its seat.

Once both the holding tire 214 and the plug 236 move off of their respective seats, the spring 196 is released and launches proximally in the direction of the push flange 202. Because they are either directly or indirectly in contact with the spring 196, the carriage 194, the needle 226, and the plug 236 are also simultaneously launched distally by the spring. The spring action thus retracts the needle 226 into the interior cavity of the plunger 190 to thereby prevent accidental contact with the needle tip (FIG. 13).

To further assist in securing the holding tire 214 against its seat, which is the mating surface area provided by the interior surface of the barrel and the base 222 of the carriage 194, in one exemplary embodiment, a projection 244 is incorporated at the shoulder 241 inside surface of the barrel 188. The raised area 244 aids in snapping the holding tire 214 in place against the spring force when the plunger is in a withdrawn position.

In one exemplary embodiment, the plunger push flange 202 is seated inside a recessed section 242 (FIGS. 12 and 13) of the enlarged barrel section 200 of the barrel 188 following the retraction of the carriage. Because the push flange 202 incorporates a smooth contour, the plunger 190 is made difficult to be grasped and moved proximally. In an alternative embodiment, a detent engagement between the barrel and the push flange may be incorporated to further deter access to the used needle.

An alternative automatic needle retract syringe 246 provided in accordance with aspects of the invention is shown in FIGS. 14, 14A and 15. The syringe 246 is substantially similar to the syringe 186 described above with reference to FIGS. 11-13 with the exception of the plunger tip 248 and plunger first tubular section 230, which are different. In the present embodiment, the plunger tip 248 incorporates a pair of extension legs 250*a*, 250*b* and the first tubular section 230 of the plunger 190 incorporates a flange 227. The extension legs 250*a*, 250*b* establish a gap or space between the exterior shoulder 234 on the plunger 190 and the plunger tip 248 when the syringe is in a ready to use position and during an injection when a distally directed force $F_D$ is applied (FIG. 14A). The flange 227 of plunger 190 first tubular section 230 is positioned at the proximal end of space 251 inside the plunger tip 248. The flange 227 secures the plunger tip 248 onto plunger 190 during aspiration of a fluid, and in one exemplary embodiment comprises a tapered face on its distal side. However, when an actuated force $F_A$ is applied on the plunger 190, the shoulder 234 bends the extension legs 250*a*, 250*b* outwardly to permit further distal movement of the plunger 190 relative to the plunger tip to retract the carriage 194 (FIG. 15). During activation, the flange 227 moves from a proximal position to a distal position within the space 251 (FIG. 15).

In the ready to retract position (FIG. 14), the plunger tip 248, plug 236, and first tubular section 230 of the plunger 190 should occupy substantially all of the head space of the variable volume chamber to minimize fluid waste. In this configuration, the plunger tip 248 should be in contact with the shoulder 252 on the barrel 188, the end tip 229 of the plunger 190 should be in contact with the holding tire 214, and the proximal end 231 of the carriage 194 should be in contact with the plug 236. Thus, as the plunger 190 is then moved distally to retract the carriage 194, the extension legs 250a, 250b are bent outwardly by the shoulder 234, the holding tire 214 and the plug 236 are moved off of their respective seats, and the spring 196 is released to expand and retract the carriage 194 (FIG. 15) into the interior cavity of the barrel 188.

FIGS. 16 and 17 show yet another alternative automatic needle retract syringe 254 provided in accordance with aspects of the present invention. The syringe 254 is substantially similar to the syringes 186, 246 described above with reference to FIGS. 11-15 with the exception of the plunger tip 256, which is different. In addition, the first tubular section 230 of the plunger 190 has been slightly modified to cooperate with the plunger tip 256, as further discussed below.

The plunger tip 256 in the present embodiment comprises a distal annular ring 258 and a proximal annular ring 260, which define a space 262 therein between. The distal and proximal annular rings 258, 260 form a size-on-size friction fit with the exterior surface of the first tubular section 230 of the plunger. Internally, a projection 264 on the first tubular portion 230 contacts the interior surface of the space 262 of the plunger tip 256. The contact between the interior surface of the space 262 and the projection 264 provide added resistance against movement of the plunger tip 256 relative to the plunger 190 during proximal movement of the plunger, i.e., during aspiration of a fluid. In addition, the projection 264 establishes a gap between the proximal annular ring 260 and the exterior shoulder 234 formed at the intersection of the first tubular portion 230 and the second tubular portion 232. Still further, the projection 264 facilitates aspirating fluid into the syringe by securing the plunger tip 256 from falling off of the first tubular portion 230 when the plunger moves proximal. Alternatively, a second projection or flange 172 (as shown in FIGS. 7 and 8) can be incorporated just proximal of the plunger tip 256, just proximal of the annular ring 260, to further secure the plunger tip 256 on the plunger 190. If incorporated, the proximal annular ring 260 of the plunger tip 256 would be secured in the gap between both projections 264 and 172.

When the plunger 190 is in position to retract the carriage 194 (FIG. 16), the plunger tip 256, plug 236, and first tubular section 230 of the plunger 190 should occupy substantially all of the head space of the variable volume chamber to minimize fluid waste. In this configuration, the plunger tip 256 should be in contact with the shoulder 252 on the barrel 188, the end tip 229 of the plunger 190 should be in contact with the holding tire 214, and the proximal end 231 of the carriage 194 should be in contact with the plug 236. Thus, as the plunger 190 is then moved distally to retract the carriage 194, the actuated force $F_A$ overcomes the friction between the plunger tip 256 and the first tubular portion 230 and allows the plunger 190 to move relative to the plunger tip 256. Concurrently therewith, the holding tire 214 and the plug 236 are moved off of their respective seats and the spring 196 is released to expand and retract the carriage 194 (FIG. 17) into the interior cavity of the barrel. In the alternative embodiment (not shown), the most proximal projection 172 (as shown in FIGS. 7 and 8) would be forced under the proximal annular ring 260 when an actuated force $F_A$ is applied.

Turning now to FIG. 18, a syringe 266 for use with a needle hub 268 having a spring loaded retractable needle 270 provided in accordance with aspects of the present invention is shown. The barrel 272 in the present embodiment comprises an integrally molded Luer tip 274 and a female lock 276 at the distal end 278 and a grip flange 280 at the proximal end 282. A plunger 284 is positioned internally of the barrel. The plunger 284 comprises an elongated tube 286 defining a bore 288, and four rectangular plates or fins 290 attached to the tube 286 with both the fins and tube attached to the push flange 292, which has an opening 294 for molding the tube 286 and a frangible seal 296 for holding an end cap 297 at the distal end of the tube (FIGS. 18 and 19). Preferably, the bore 288 has a greater inside diameter than the end cap 297, for reasons explained below. The opening 294 is then sealed with a plug 298. The plunger 284 also includes a push plate 300 and a distally projecting tip holder 302, which is located proximal of an extension pin 304, and which makes up part of the tube 286. The extension pin 304 is sized to fit within the Luer tip 274, which is sized to receive the needle hub 268, as further discussed below. In one exemplary embodiment, the elongated tube 286 is cylindrical in shape. However, other elongated shaped bodies may be incorporated without deviating from the scope of the present invention.

The plunger tip 308 comprises an opening 310 for accommodating the extension pin 304, a proximal annular ring 312 forming a size-on-size friction fit with the tip holder 302, and a pair of proximally extending extension legs 314a, 314b. In one exemplary embodiment, the extension legs 314a, 314b and the annular ring 312 contact both the push plate 300 and the tip holder plate 316. However, a small gap between the annular ring 312 and the tip holder plate 316 is acceptable.

In one exemplary embodiment, the needle hub 268 useable with the syringe 266 of the present embodiment comprises a housing 318, which comprises a distal housing structure 320 having a needle 270 protruding therefrom, a proximal housing structure 322 having male threads 320 thereon for threaded engagement with the female lock 276, a central activation compartment 324 disposed therebetween, and a bore 326 defined therethrough. A generally cylindrical tube 323 with optional support fins 325 are located at the distal end of the needle hub 268. The bore 326 extends through the cylindrical tube 323 and has a size sufficient to accommodate the needle 270 and a spring 327, as further discussed below. At the distal end of the cylindrical tube 323 is an annular cap 329 having a close tolerance fit with the outside diameter of the needle 270. The annular cap 329 provides an anchor and supports one end of the spring 327, as further discussed below.

Exteriorly, the housing 318 is tapered inwardly in the direction from the proximal housing structure 322 towards the distal housing structure 320, although a straight cylinder or wall may be acceptable. At the central activation compartment 324, the housing incorporates two wells 328a, 328b (FIG. 19), which form two thin-walled sections 330 with the bore 326 of the hub 268. The thin-walled sections 330 each include a bulge section 332 that forms a receiving space inside the bore 326 for mating engagement with the needle sleeve 334, as further discussed below. Referring to FIG. 19 in addition to FIG. 18, the thin-walled sections 330 of the wells 328a, 328b each includes a base section 336, a transition section 338, which is tapered or angled from the base section, and a gripping section 340, where the bulge 332 is located. Alternatively, a single well with a single thin-walled section may be incorporated in the needle hub.

The needle sleeve 334 (FIG. 19) comprises a generally elongated tube that includes a bulge section 342 and a bore. In one exemplary embodiment, the exterior surface 344 of the sleeve 334 comprises an undulating surface for increased gripping engagement with the gripping sections 340 of the wells 328a, 328b. To secure the needle 270 to the sleeve 334, the sleeve bore comprises a glue well 346 for gluing the needle to the sleeve (FIG. 19).

To assemble the needle hub 268, the spring 327 is first mounted over the combination needle 270 and needle sleeve 334. The needle 270 and spring 327 are then inserted into the bore 326 of the needle hub 268 from the proximal end opening of the hub. The needle 270 is pushed distally through the bore 326 until the needle sleeve 334 engages the gripping section 340 of the needle hub, at the two wells 328a, 328b. In one exemplary embodiment, the engagement is achieved when the bulge 342 on the sleeve 334 fits into the space provided by the bulge 332 of the gripping section 240.

To retract the needle 270, the plunger 284 is first moved distally with a distally directed force $F_D$ until the distal end surface of the plunger tip 308 contacts the shoulder or end 348 of the barrel 272. At this point, the extension pin 304 is positioned inside the Luer tip 274 with the end cap 297 on the extension pin 304 slightly spaced apart from the proximal end 350 of the needle 270 (FIG. 19). As an actuated force $F_A$ is then applied to the plunger 284, the push plate 300 moves distally to bend the extension legs 314a, 314b inwardly (or outwardly if the extensions legs 314a, 314b were positioned closer to the tip holder 302). Concurrently therewith, the extension pin 304 moves forward and causes the transition section 338 of the wells 328a, 328b to deform outwardly to separate from the bulge 342 on the needle sleeve 334. The forward motion also pushes the end cap 297 of the extension pin 304 against the proximal end 350 of the needle 270. Because the needle 270 is anchored by the needle sleeve 334 abutting against the hub 268, the needle 270 pushes back against the end cap 297 with an equal but opposite force and causes the frangible seal 296 to tear or separate. The proximal end 350 of the needle 270 eventually completely tears the end cap 297 from the extension pin 304, which then provides a passage for the spring 327 to expand. The expanding spring 327 then pushes the needle sleeve 336 proximally, which is attached to the needle 270 and pushes the needle proximally into the bore 288 located in the plunger 284 to thereby prevent accidental contact with the needle tip. Once the needle is retracted, the syringe may be safely disposed of per normal protocols.

As best shown in FIGS. 18 and 20, when the actuated force $F_D$ is applied to the plunger 284 to retract the needle 270, the plunger moves distally relative to the plunger tip 308. As discussed above, this relative movement is provided by a gap between the tip holder plate 316 of the syringe tip holder 302 and the end surface 313 of the plunger tip 308. Said gap should be of sufficient dimension so as to not delimit the proximal end 350 of the needle 270 from puncturing the frangible seal 296.

Referring now to FIG. 21, an alternative syringe 352 for use with a needle hub 268 having a spring loaded retractable needle 270 provided in accordance with aspects of the present invention is shown. The syringe 352 is substantially similar to the syringe 266 described above with reference to FIGS. 18-20 with the exception of the plunger tip 354, which is different. In addition, the tip holder 356 of the plunger 284 has been slightly modified to cooperate with the plunger tip 354, as further discussed below.

The plunger tip 354 in the present embodiment comprises an internal bore 358 comprising an internal diameter sized to frictionally engage the exterior surface of the tip holder 356. As before, a gap for relative movement between the plunger tip 354 and the plunger 284 are provided inside the plunger tip bore, between the distal end of the tip holder 356 and the end surface 360 of the plunger tip 354. The proximal end of the plunger tip 354 abuts the push plate 300 on the plunger 284. This contact enables the push plate 300 to move the plunger tip 354 distally when a distally directed force $F_D$ is applied, and to compress the plunger tip to retract the needle 270 when an actuated force $F_A$ is applied. The mechanism for retracting the needle 270 for the needle hub 268 is the same as that discussed above with reference to the needle hub of FIGS. 18-20.

Turning now to FIG. 22, an alternative syringe 362 for use with a needle hub 268 having a spring loaded retractable needle 270 provided in accordance with aspects of the present invention is shown. The syringe 362 is substantially similar to the syringes 266, 352 described above with reference to FIGS. 18-21 with the exception of the plunger tip 364, which is different. In addition, the tip holder 366 of the plunger 284 has been slightly modified to cooperate with the plunger tip 364, as further discussed below.

In the present embodiment, the plunger tip 364 incorporates a groove 368 in the interior bore 358 of the plunger tip. The groove 368 is sized to receive a plunger disc 370 on the plunger 284 and allows it to move distally upon application of an actuated force $F_A$ as described below. In one exemplary embodiment, the pusher plate 300 is located apart from the proximal annular ring 372 of the plunger tip 364 when in the ready to use position.

To retract the needle 270, the plunger is first advanced from a proximal to a distal position shown in FIG. 22. At this position, the end surface 360 of the plunger tip 364 contacts the end shoulder 348 of the barrel 272. When an actuated force $F_A$ is then applied to the plunger 284, the plunger disc 370 moves distally within groove 368 of the plunger tip 364 and the plunger 284 moves distally relative to the end surface 360 of the plunger tip. The pusher plate 300 moves to meet the proximal annular ring 372 of the plunger tip 364. Concurrently therewith, the extension pin 304 contacts the needle 270 to retract the needle as discussed above with reference to FIGS. 18-20.

Turning now to FIG. 23, a partial cross-sectional view of an alternative needle hub 374 provided in accordance with aspects of the present invention is shown. The needle hub 374 is substantially similar to the needle hub 268 described above with reference to FIGS. 18-20 with the exception of the way in which the gripping section 340 of the wells 328a, 328b of the needle hub grips the needle 376. The needle hub 374 may be used with any of the syringes 266, 352, 362 described above with reference to FIGS. 18, 21, and 22 and may be actuated to retract the needle 376 the same way as described with those syringes 266, 352, 362. However, instead of utilizing a needle sleeve 334 (FIG. 19), in the present embodiment, the proximal end of the needle 376 incorporates a crimp or a bulge 378. The bulge or crimp 378 may be made by pinching the needle to create a crimp or by a controlled compression process to create a bulge.

The needle hub 374 may be assembled by first positioning a spring 327 over the needle 376, which then rests on an end against the bulge or crimp 378. The combination needle 376 and spring 327 is then inserted into the bore 326 of the needle hub and pushed distally until the bulge or crimp 378 engages with the space provided by the bulge 332 formed in the thin-walled sections 330 of the wells 328a. 328b. Once engaged, the crimp or bulge 378 and the annular ring or cap 329 on the tube section 323 of the needle hub (See, e.g. FIG. 18) compresses the spring and loads the needle 376 for retraction.

Although limited embodiments of the syringe assemblies and their components have been specifically described and illustrated herein, many modifications and variations will be apparent to those skilled in the art. Accordingly, it is to be understood that the syringe assemblies and their components constructed according to principles of this invention may be embodied other than as specifically described herein. The invention is defined in the following claims.

What is claimed is:

1. A syringe comprising:
a barrel including a gripping flange at a proximal end, an end wall at a distal end defining an opening, an internal shoulder at a location spaced from the end wall, and a sidewall structure comprising an exterior surface and an interior surface defining an interior cavity;
a plunger including a tubular body having a shoulder, an interior cavity disposed in the interior cavity of the barrel, a push flange at a proximal end, and a plunger tip holder including a push end;
an elastomeric plunger tip mounted on the elastomeric plunger tip holder, the plunger tip having a hollow space such that a hollow cavity is defined by an interior surface of the elastomeric plunger tip and the plunger tip holder;
a carriage including an elongated body having a spring located thereon, a base extending from the elongated body, a shoulder positioned between the elongated body and the base, and a passage receiving a needle;
wherein the spring is compressed by the end wall of the barrel and the shoulder on the carriage and the carriage is removably and frictionally secured to the barrel by a resilient holding tire wedged between the base of the carriage and the interior surface of the barrel;
wherein the plunger comprises three plunger positions including a first plunger position in which the elastomeric plunger tip is spaced apart from the carriage, a second plunger position in which the elastomeric plunger tip simultaneously contacts the shoulder on the tubular body and the internal shoulder on the barrel while the resilient holding tire is positioned on the base of the carriage, and a third plunger position in which the push end on the plunger has pushed the resilient holding tire distally off of the base of the carriage; and
wherein the elastomeric plunger tip and the plunger are movable relative to one another when the plunger moves from the second plunger position to the third plunger position.

2. The syringe of claim 1, wherein in the second plunger position the internal shoulder on the barrel stops the elastomeric plunger tip from further distal movement toward the barrel distal end.

3. The syringe of claim 1, wherein the elastomeric plunger tip comprises an extension leg that extends proximally from a proximal annular ring of the elastomeric plunger tip to abut the shoulder on the plunger.

4. The syringe of claim 1, wherein when the elastomeric plunger tip comprises a proximal end wall and wherein the push flange of the plunger moves relative to the proximal end wall of the elastomeric plunger tip in moving from the second plunger position to the third plunger position.

5. The syringe of claim 1, wherein the plunger tip holder comprises a flange that moves inside the hollow cavity when the plunger moves from the second plunger position to the third plunger position.

6. The syringe of claim 1, wherein the spring launches proximally into the interior cavity of the tubular body of the plunger when the plunger is in the third plunger position.

7. The syringe of claim 1, further comprising a plug positioned at a distal end of the interior cavity of the tubular body of the plunger.

8. The syringe of claim 7, wherein the plug comprises a frontal projection and a larger base portion relative to the frontal projection.

9. The syringe of claim 1, wherein the plunger is moved from the first plunger position to the second position when a distally directed force is applied to the push flange, and from the second plunger position to the third plunger position when an actuated force is applied to the push flange, and wherein the actuated force is greater than the distally directed force.

10. The syringe of claim 1, wherein the plunger is disposed in the interior cavity of the barrel along a first interior surface section of the barrel, the resilient holding tire is wedged between the base of the carriage and a second interior surface section of the barrel, and the first interior surface section of the barrel has a larger diameter than the second interior surface section of the barrel.

11. The syringe of claim 10, wherein the internal shoulder on the barrel extends from the first interior surface section of the barrel to the second interior surface section of the barrel.

12. A syringe comprising:
a barrel including a gripping flange at a proximal end, an end wall at a distal end defining an opening, an internal shoulder at a location spaced from the end wall, and a sidewall structure comprising an exterior surface and an interior surface defining an interior cavity;
a plunger including a tubular body having an interior cavity disposed in the interior cavity of the barrel, a push flange at a proximal end, and a plunger tip holder, the plunger tip holder including a push end, a shoulder defining a boundary between a relatively greater diameter portion and relatively lesser diameter portion, and a radially outward projection located distal of the shoulder;
an elastomeric plunger tip mounted on the relatively lesser diameter portion of the elastomeric plunger tip holder, the plunger tip including a proximal annular ring, a distal annular ring, and a contoured outer surface between the proximal annular and the distal annular ring that does not contact the interior surface, wherein the elastomeric plunger tip comprises a hollow space such that a hollow cavity is defined by an interior surface of the elastomeric plunger tip and the plunger tip holder;
a carriage including an elongated body having a spring located thereon, a base extending from the elongated body, a shoulder positioned between the elongated body and the base, and a passage receiving a needle;
wherein the spring is compressed by the end wall of the barrel and the shoulder on the carriage and the carriage is removably and frictionally secured to the barrel by a resilient holding tire wedged between the base of the carriage and the interior surface of the barrel;
wherein the plunger comprises three plunger positions including a first plunger position in which the elastomeric plunger tip is spaced apart from the carriage, a second plunger position in which the elastomeric plunger tip contacts the internal shoulder on the barrel and the radially outward projection on the plunger contacts the proximal annular ring on the elastomeric plunger tip while the resilient holding tire is positioned on the base of the carriage, and a third plunger position in which the push end on the plunger has pushed the resilient holding tire distally off of the base of the carriage, the radially outward projection on the plunger contacts the distal annular ring on the elastomeric plunger tip, and the shoulder on the plunger contacts the proximal annular ring on the elastomeric plunger tip; and wherein the elastomeric plunger tip and the plunger are movable relative to one another when the plunger moves from the second plunger position to the third plunger position.

13. The syringe of claim 12, wherein in the second plunger position, the internal shoulder on the barrel stops the elastomeric plunger tip from further distal movement toward the barrel distal end.

14. The syringe of claim 12, wherein the push flange moves relative to the elastomeric plunger tip proximal annular ring when the plunger moves from the second plunger position to the third plunger position.

15. The syringe of claim 12, wherein the spring launches proximally into the interior cavity of the tubular body of the plunger when the plunger is in the third plunger position.

16. The syringe of claim 12, further comprising a plug positioned at a distal end of the interior cavity of the tubular body of the plunger.

17. The syringe of claim 16, wherein the plug comprises a frontal projection and a larger base portion relative to the frontal projection.

18. The syringe of claim 17, wherein the base portion of the plug is compressed by a wall surface of the tubular body.

19. The syringe of claim 12, wherein the plunger is moved from the first plunger position to the second position when a distally directed force is applied to the push flange, and from the second plunger position to the third plunger position when an actuating force is applied to the push flange, and wherein the actuating force is greater than the distally directed force.

20. The syringe of claim 12, wherein the plunger is disposed in the interior cavity of the barrel along a first interior surface section of the barrel, the resilient holding tire is wedged between the base of the carriage and a second interior surface section of the barrel, and the first interior surface section of the barrel has a larger diameter than the second interior surface section of the barrel.

21. The syringe of claim 20, wherein the internal shoulder on the barrel extends from the first interior surface section of the barrel to the second interior surface section of the barrel.

22. A syringe comprising:
a barrel including a gripping flange at a proximal end, an end wall at a distal end defining an opening, an internal shoulder at a location spaced from the end wall, and a sidewall structure comprising an exterior surface and an interior surface defining an interior cavity;
a plunger including a tubular body having an interior cavity disposed in the interior cavity of the barrel, a push flange at a proximal end, and a plunger tip holder, the plunger tip holder including a push end and a shoulder defining a boundary between a greater diameter portion and a lesser diameter portion;
an elastomeric plunger tip mounted on the lesser diameter portion of the plunger tip holder, the elastomeric plunger tip comprising a proximal end face and a distal end face, wherein the elastomeric plunger tip comprises a hollow space such that a hollow cavity is defined by an interior surface of the elastomeric plunger tip and the plunger tip holder;
a carriage including an elongated body having a spring located thereon, a base extending from the elongated body, a shoulder positioned between the elongated body and the base, and a passage receiving a needle;
wherein the spring is compressed by the end wall of the barrel and the shoulder on the carriage and the carriage is removably and frictionally secured to the barrel by a resilient holding tire wedged between the base of the carriage and the interior surface of the barrel;
wherein the push flange is movable distally relative to the proximal end face of the elastomeric plunger tip after the elastomeric plunger tip contacts the internal shoulder on the barrel.

23. The syringe of claim 22, wherein the elastomeric plunger tip comprises a proximal annular ring and a distal annular ring, the proximal and distal annular rings having the same internal diameter.

24. The syringe of claim 22, wherein the elastomeric plunger tip being shaped as a smoothly tapered cylinder having a constant inner diameter between a proximal end and a distal end and having a greater wall thickness at the proximal and distal ends and a lesser wall thickness at locations in between the proximal and distal ends, the proximal end abutting the shoulder on the tubular body of the plunger.

* * * * *

UNITED STATES PATENT AND TRADEMARK OFFICE
CERTIFICATE OF CORRECTION

PATENT NO. : 8,758,296 B2  
APPLICATION NO. : 12/433553  
DATED : June 24, 2014  
INVENTOR(S) : Woehr et al.

Page 1 of 1

It is certified that error appears in the above-identified patent and that said Letters Patent is hereby corrected as shown below:

In the Specification

In column 3, line 49, delete "position." and insert -- position; --, therefor.

In column 9, line 31, delete "1118b" and insert -- 118b --, therefor.

In column 16, line 63, delete "328a." and insert -- 328a, --, therefor.

In column 16, line 65, delete "e.g." and insert -- e.g., --, therefor.

In the Claims

In column 18, lines 38-39, claim 12, delete "the elastomeric plunger tip holder, the plunger tip" and insert -- the plunger tip holder, the elastomeric plunger tip --, therefor.

In column 18, line 42, claim 12, delete "surface," and insert -- surface of the barrel, --, therefor.

Signed and Sealed this  
Twenty-eighth Day of October, 2014

Michelle K. Lee  
*Deputy Director of the United States Patent and Trademark Office*